United States Patent

Chin et al.

[11] Patent Number: 5,672,567
[45] Date of Patent: Sep. 30, 1997

[54] HERBICIDAL HYDROXYBENZYL-SUBSTITUTED HETEROARYL COMPOUNDS AND DERIVATIVES THEREOF

[75] Inventors: Hsiao-Ling M. Chin, Moraga; Yi-Qiu Wei, Pinole; Nhan H. Nguyen, Richmond; David B. Kanne, Corte Madera, all of Calif.

[73] Assignee: Zeneca Limited, London, England

[21] Appl. No.: 622,179

[22] Filed: Mar. 25, 1996

Related U.S. Application Data

[63] Continuation of Ser. No. 236,309, May 2, 1994, abandoned.

[51] Int. Cl.$^6$ .......................... A01N 43/54; C07D 239/26
[52] U.S. Cl. .......................... 504/239; 504/242; 504/243; 544/243; 544/298; 544/302; 544/335
[58] Field of Search .......................... 504/239, 242, 504/243; 544/298, 302, 322, 309, 315, 319, 243, 335

[56] References Cited

U.S. PATENT DOCUMENTS

| | | | |
|---|---|---|---|
| 4,116,665 | 9/1978 | Krumkalns | 504/132 |
| 4,407,806 | 10/1983 | Cherpeck | 424/263 |
| 4,417,050 | 11/1983 | Cherpeck | 544/335 |
| 5,055,476 | 10/1991 | Effland et al. | 514/338 |
| 5,308,826 | 5/1994 | Chin et al. | 504/132 |

FOREIGN PATENT DOCUMENTS

| | | |
|---|---|---|
| 0 289 380 | 11/1988 | European Pat. Off. |
| 0 489 670 | 6/1992 | European Pat. Off. |
| 19 13 726 | 10/1969 | Germany |
| 33 03 741 | 8/1984 | Germany |
| 95 01968 | 1/1995 | WIPO |

OTHER PUBLICATIONS

J. Chem. Soc. Perkin Tras I, 1988, 3085–96.

Ple et al., *Tetrahedron Letters*, "Metalation of Diazines VIII", vol. 34, No. 10, 1993, Oxford GB, pp. 1605–1608.

Ple et al., *Journal of Heterocyclic Chemicstry*, "Metalation of Diazines. XI.", vol. 31, Nov. 1994, Provo US, pp. 1311–1315.

Ple et al., *Journal of Heterocyclic Chemistry*, "Metallation of Diazines. III.", vol. 28, Feb. 1991, Provo US, pp. 283–287.

Ple et al., *Journal of Heterocyclic Chemistry*, "Metallation of Diazines.V.", vol. 29, Mar. 1992, Provo US, pp. 467–470.

Chemical Abstracts, vol. 59, No. 1, 1963, Columbus, Ohio, US; col. 8739A, Rajkumar et al., "*Synthesis of 5-Substituted Pyrimidines*".

*Primary Examiner*—Yogendra N. Gupta
*Attorney, Agent, or Firm*—Joseph R. Snyder; Marian T. Thomson

[57] ABSTRACT

Herbicidal substituted hydroxybenzyl-heteroaryl compounds and derivatives thereof of the formula

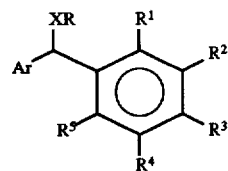

wherein Ar is a substituted or unsubstituted 5- or 6-membered heteroaryl group having 2 or 3 ring nitrogen atoms or a substituted or unsubstituted 5-membered heteroaryl group having two ring heteroatoms, one of the ring heteroatoms being nitrogen and the other being sulfur or oxygen. Herbicidal compositions containing such substituted hydroxybenzyl-heteroaryl compounds and derivatives thereof and methods of controlling undesirable vegetation employing these compounds and derivatives are also disclosed. The compounds in which XR is hydroxyl are also useful as intermediates for producing the disclosed substituted hydroxybenzyl-heteroaryl derivatives.

15 Claims, No Drawings

HERBICIDAL HYDROXYBENZYL-SUBSTITUTED HETEROARYL COMPOUNDS AND DERIVATIVES THEREOF

This application is a continuation of application Ser. No. 08/236,309, filed May 2, 1994 abandoned.

FIELD OF THE INVENTION

In one aspect, this invention relates to novel hydroxybenzyl-substituted nitrogen-containing heteroaryl compounds and derivatives thereof which exhibit unexpectedly desirable herbicidal activity. In other aspects, this invention relates to herbicidal compositions comprising a hydroxybenzyl-substituted nitrogen-containing heteroaryl compound or derivative thereof and a suitable carrier, to a method of controlling undesirable vegetation comprising applying to the area where control is desired an herbicidally effective amount of a hydroxybenzyl-substituted nitrogen-containing heteroaryl compound or derivative thereof and to intermediates useful in making such compounds.

BACKGROUND OF THE INVENTION

The need for effective herbicides needs no special emphasis. The control of weeds and undesirable vegetation is of great economic importance since weed competition inhibits the production of foliage, fruit or seed of agricultural crops. The presence of weeds can reduce harvesting efficiency and the quality of the harvested crop. Weeds on noncropped areas may cause a fire hazard, undesirable drifting of sand or snow, and/or irritation to persons with allergies. Thus, suppression of undesirable weed growth is very advantageous.

Accordingly, it is an object of this invention to provide effective novel herbicidal compounds, as well as to provide novel herbicidal compositions and novel methods of controlling weeds. Further, it is an object of this invention to provide intermediates which, as well as exhibiting herbicidal activity, are also useful in the production of other herbicidally active compounds.

While certain hydroxybenzyl-substituted nitrogen-containing heteroaryl compounds are disclosed in the art, these disclosures contain no description of the utility of such compounds. Thus, Radinov et al., "Synthesis of 4-Amino-3-pyridinyl and 4-Amino-5-pyrimidinyl Aryl Ketones and Related Compounds via an ortho-Lithiation Reaction", Synthesis, pp. 886–891 (November 1986), disclose inter alia at page 887, compounds of the formula

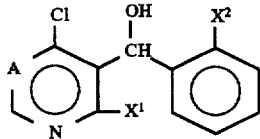

wherein A is CH or N, and when A is CH, $X^1$ is H and $X^2$ is hydrogen, chlorine or fluorine, and when A is N, $X^1$ is chlorine and $X^2$ is hydrogen.

Somewhat similarly, Marsais et al., "Directed Lithiation of 4-Halopyridines: Chemoselectivity, Regio-selectivity and Application to Synthesis", J. Heterocyclic Chem., Vol 25, pp. 81–87 (1987), disclose the production of compounds of the formula

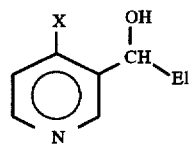

wherein El is phenyl or 2-methoxyphenyl.

Certain (non-substituted)-pyridyl-3-carbinols of the formula

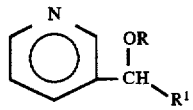

are disclosed in U.S. Pat. No. 4,407,806 to Cherpeck (wherein R and $R^1$ are as defined therein).

Similarly, U.S. Pat. No. 4,116,665 to Krumkalns discloses a method of regulating the growth of aquatic weeds employing compounds of the formula

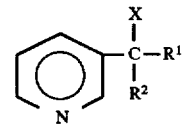

wherein, inter alia, $R^1$ may be hydrogen, $R^2$ may be (substituted)-phenyl and X may be hydroxyl or alkoxy.

Further, commonly owned U.S. application Ser. No. 08/051,490, filed Apr. 22, 1993, describes herbicidal 4-substituted pyridyl-3-carbinols.

SUMMARY OF THE INVENTION

In one aspect, this invention is directed to a compound of the formula (I):

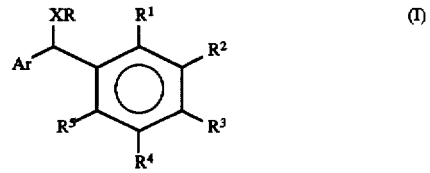

wherein:

Ar is a substituted or unsubstituted 5- or 6-membered heteroaryl group having 2 or 3 ring nitrogen atoms or a substituted or unsubstituted 5-membered heteroaryl group having two ring heteroatoms, one of the ring heteroatoms being nitrogen and the other ring heteroatom being sulfur or oxygen, and the remainder of the ring atoms being carbon;

$R^1$, $R^2$, $R^3$, $R^4$ and $R^5$ are each independently hydrogen, halogen, $C_1$–$C_6$ alkyl, $C_2$–$C_6$ alkenyl, $C_2$–$C_6$ alkynyl, nitro, cyano, hydroxy, thiocyano, —N($R^{11}$)($R^{12}$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)-alkyl, halo($C_1$–$C_6$)alkoxy-($C_1$–$C_6$)alkyl, —C(X)—$R^{10}$ or —S(O)$_k$—$R^{10}$;

X is oxygen or sulfur;

R is hydrogen, hydrocarbyl, hydrocarbyl substituted with one or more of halogen or $C_1$–$C_6$ alkoxy or is of the formula —C(Y)—$R^6$, —C(O)—C(O)—$R^6$, —S(O)$_2$—$R^6$, —P(Y)($R^{11}$)($R^{12}$) or —Si($R^{13}$)($R^{14}$)($R^{15}$);

wherein:

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S— or is of the formula —N($R^7$)($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl($C_1$–$C_6$)alkyl, hydroxycarbonyl($C_1$–$C_6$)alkyl, or N($R^9$)—($R^{10}$) wherein $R^9$ and $R^{10}$ are each independently hydrogen, $C_1$–$C_6$ alkyl or phenyl;

or $R^7$ and $R^8$ together with the nitrogen to which they are bound form an aziridine, piperazine, morpholine, thiomorpholine, thiomorpholine 1-oxide, thiomorpholine 1-1, dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_1$–$C_6$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl; and k is 0, 1 or 2;

and agriculturally acceptable salts thereof;

with the proviso that when R is H, at least one of $R^1$, $R^2$, $R^3$, $R^4$ and $R^5$ is not hydrogen.

In another aspect, this invention is directed to a herbicidal composition comprising:

(A) a compound of the formula (I):

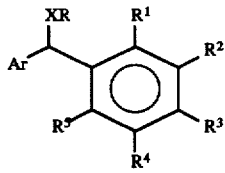

wherein:

Ar is a substituted or unsubstituted 5- or 6-membered heteroaryl group having 2 or 3 ring nitrogen atoms or a substituted or unsubstituted 5-membered heteroaryl group having two ring heteroatoms, one of the ring heteroatoms being nitrogen and the other ring heteroatom being sulfur or oxygen, and the remainder of the ring atoms being carbon;

$R^1$, $R^2$, $R^3$, $R^4$ and $R^5$ are each independently hydrogen, halogen, $C_1$–$C_6$ alkyl, $C_2$–$C_6$ alkenyl, $C_2$–$C_6$ alkynyl, nitro cyano, hydroxy, thiocyano, —N($R^{11}$)($R^{12}$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$)alkoxy-($C_1$–$C_6$)alkyl, —C(X)—$R^{10}$ or —S(O)$_k$—$R^{10}$;

X is oxygen or sulfur;

R is hydrogen, hydrocarbyl, hydrocarbyl substituted with one or more of halogen or $C_1$–$C_6$ alkoxy or is of the formula —C(Y)—$R^6$, —C(O)—C(O)—$R^6$, —S(O)$_2$—$R^6$, —P(Y)($R^{11}$)($R^{12}$) or —Si($R^{13}$)($R^{14}$)($R^{15}$);

wherein:

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S— or is of the formula —N($R^7$)($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl ($C_1$–$C_6$)alkyl, hydroxycarbonyl($C_1$–$C_6$)alkyl, or N($R^9$)—($R^{10}$) wherein $R^9$ and $R^{10}$ are each independently hydrogen, $C_1$–$C_6$ alkyl or phenyl;

or $R^7$ and $R^8$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_1$–$C_6$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl; and k is 0, 1 or 2;

or an agriculturally acceptable salt thereof; and (B) a carrier therefor.

In yet another aspect, this invention is directed to a method for controlling undesirable vegetation comprising applying to the area where control is desired an herbicidally effective amount of a compound of the formula (I):

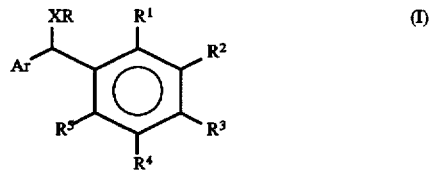

wherein:

Ar is a substituted or unsubstituted 5- or 6-membered heteroaryl group having 2 or 3 ring nitrogen atoms or a substituted or unsubstituted 5-membered heteroaryl group having two ring heteroatoms, one of the ring heteroatoms being nitrogen and the other ring heteroatom being sulfur or oxygen, and the remainder of the ring atoms being carbon;

$R^1$, $R^2$, $R^3$, $R^4$ and $R^5$ are each independently hydrogen, halogen, $C_1$–$C_6$ alkyl, $C_2$–$C_6$ alkenyl, $C_2$–$C_6$ alkynyl, nitro, cyano, hydroxy, thiocyano, —N($R^{11}$)($R^{12}$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$)alkoxy-($C_1$–$C_6$)alkyl, —C(X)—$R^{10}$ or —S(O)$_k$—$R^{10}$;

X is oxygen or sulfur;

R is hydrogen, hydrocarbyl, hydrocarbyl substituted with one or more of halogen or $C_1$–$C_6$ alkoxy or is of the formula —C(Y)—$R^6$, —C(O)—C(O)—$R^6$, —S(O)$_2$—$R^6$, —P(Y)($R^{11}$)($R^{12}$) or —Si($R^{13}$)($R^{14}$)$R^{15}$; wherein:

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S— or is of the formula —N($R^7$)($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl($C_1$–$C_6$)alkyl, hydroxycarbonyl($C_1$–$C_6$)alkyl, or N($R^9$)($R^{10}$) wherein $R^9$ and $R^{10}$ are each independently hydrogen, $C_1$–$C_6$ alkyl or phenyl;

or $R^7$ and $R^8$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolidine ring, any of which may be optionally substituted with $C_1$-$C_6$ alkyl;

$R^{11}$ and $R^{12}$ are each independently $C_1$-$C_6$ alkyl, $C_1$-$C_6$ alkylthio or $C_1$-$C_6$ alkoxy;

$R^{13}$, $R^{14}$ and $R^{15}$ are each independently $C_1$-$C_6$ alkyl, $C_1$-$C_6$ alkoxy, $C_1$-$C_6$ haloalkyl, aryl or arylalkyl; and k is 0, 1 or 2;

or an agriculturally acceptable salt thereof.

In yet a further aspect, because the compounds of this invention wherein XR is OH are useful intermediates for producing the other compounds of this invention, as well as possessing herbicidal activity, this invention is directed to compounds of the formula (II):

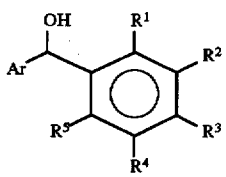

wherein:

Ar is a substituted or unsubstituted 5- or 6-membered heteroaryl group having 2 or 3 ring nitrogen atoms or a substituted or unsubstituted 5-membered heteroaryl group having two ring heteroatoms, one of the ring heteroatoms being nitrogen and the other ring heteroatom being sulfur or oxygen, and the remainder of the ring atoms being carbon;

$R^1$, $R^2$, $R^3$, $R^4$ and $R^5$ are each independently hydrogen, halogen, $C_1$-$C_6$ alkyl, $C_2$-$C_6$ alkenyl, $C_2$-$C_6$ alkynyl, nitro, cyano, hydroxy, thiocyano, —N($R^{11}$)($R^{12}$), $C_1$-$C_6$ haloalkyl, $C_1$-$C_6$ alkoxy, $C_1$-$C_6$ haloalkoxy, ($C_1$-$C_6$)alkoxy-($C_1$-$C_6$)alkyl, halo($C_1$-$C_6$)alkoxy-($C_1$-$C_6$)alkyl, —C(X)—$R^{10}$ or —S(O)$_k$—$R^{10}$, with the proviso that at least one of $R^1$, $R^2$, $R^3$, $R^4$ and $R^5$ is not hydrogen;

$R^{10}$ is hydrogen, $C_1$-$C_6$ alkyl or phenyl;

$R^{11}$ and $R^{12}$ are each independently $C_1$-$C_6$ alkyl, $C_1$-$C_6$ alkylthio or $C_1$-$C_6$ alkoxy; and k is 0, 1 or 2;

and agriculturally acceptable salts thereof.

DETAILED DESCRIPTION OF THE PREFERRED EMBODIMENTS

The novel herbicidal compounds of this invention are of the formula (I):

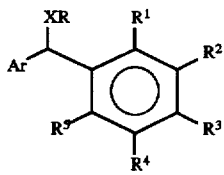

wherein:

Ar is a substituted or unsubstituted 5- or 6-membered heteroaryl group having 2 or 3 ring nitrogen atoms or a substituted or unsubstituted 5-membered heteroaryl group having two ring heteroatoms, one of the ring heteroatoms being nitrogen and the other ring heteroatom being sulfur or oxygen, and the remainder of the ring atoms being carbon;

$R^1$, $R^2$, $R^3$, $R^4$ and $R^5$ are each independently hydrogen, halogen, $C_2$-$C_6$ alkyl, $C_2$-$C_6$ alkenyl, $C_1$-$C_6$ alkynyl, nitro, cyano, hydroxy, thiocyano, —N($R^{11}$)($R^{12}$), $C_1$-$C_6$ haloalkyl, $C_1$-$C_6$ alkoxy, $C_1$-$C_6$ haloalkoxy, ($C_1$-$C_6$) alkoxy-($C_1$-$C_6$)alkyl, halo($C_1$-$C_6$)alkoxy-($C_1$-$C_6$)alkyl, —C(X)—$R^{10}$ or —S(O)$_k$—$R^{10}$;

X is oxygen or sulfur;

R is hydrogen, hydrocarbyl, hydrocarbyl substituted with one or more of halogen or $C_1$-$C_6$ alkoxy or is of the formula —C(Y)—$R^6$, —C(O)—C(O)—$R^6$, —S(O)$_2$—$R^6$, —P(Y)($R^{11}$)($R^{12}$) or —Si($R^{13}$)($R^{14}$)($R^{15}$);

wherein:

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S— or is of the formula —N($R^7$)($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$-$C_6$)alkoxycarbonyl($C_1$-$C_6$)alkyl, hydroxycarbonyl($C_1$-$C_6$)alkyl, or N($R^9$)—($R^{10}$) wherein $R^9$ and $R^{10}$ are each independently hydrogen, $C_1$-$C_6$ alkyl or phenyl;

or $R^7$ and $R^8$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolidine ring, any of which may be optionally substituted with $C_1$-$C_6$ alkyl;

$R^{11}$ and $R^{12}$ are each independently $C_1$-$C_6$ alkyl, $C_1$-$C_6$ alkylthio or $C_1$-$C_6$ alkoxy;

$R^{13}$, $R^{14}$ and $R^{15}$ are each independently $C_1$-$C_6$ alkyl, $C_1$-$C_6$ alkoxy, $C_1$-$C_6$ haloalkyl, aryl or arylalkyl; and k is 0, 1 or 2;

and agriculturally acceptable salts thereof;

with the proviso that when R is hydrogen, at least one of $R^1$, $R^2$, $R^3$, $R^4$ and $R^5$ is not hydrogen.

Preferably,

Ar is a substituted or unsubstituted pyrimidinyl, pyrazinyl, triazolyl, imidazolyl or thiazolyl group;

$R^1$, $R^2$, $R^3$, $R^4$ and $R^5$ are each independently hydrogen, halogen, $C_1$-$C_6$ alkyl, $C_1$-$C_6$ haloalkyl, $C_1$-$C_6$ alkoxy, $C_1$-$C_6$ haloalkoxy, nitro or —S(O)$_k$—($C_1$-$C_3$)alkyl wherein k is 0, 1 or 2; and R is of the formula

wherein $R^6$ is $C_1$-$C_{12}$ alkyl, $C_1$-$C_6$ haloalkyl, phenyl or is N($R^7$)($R^8$), wherein $R^7$ and $R^8$ are each independently $C_1$-$C_{12}$ alkyl, hydrogen, $C_2$-$C_{12}$ alkenyl, $C_2$-$C_{12}$ alkynyl, $C_1$-$C_{12}$ haloalkyl, $C_1$-$C_6$ alkoxy, ($C_1$-$C_6$)alkoxy($C_1$-$C_6$) alkyl or $R^7$ and $R^8$ together with the nitrogen to which they are bound form a morpholine, piperidine or pyrrolidine ring.

More preferably,

Ar is a substituted or unsubstituted pyrimidinyl, pyrazinyl, triazolyl, imidazolyl or thiazolyl group;

$R^1$ is hydrogen, trifluoromethyl, fluoro, chloro, bromo, iodo, methoxy, methyl or ethyl;

$R^2$, $R^3$, $R^4$ and $R^5$ are each independently hydrogen, chloro or bromo;

X is oxygen; and

R is of the formula $$-\overset{O}{\underset{\|}{C}}-R^6$$

wherein $R^6$ is $C_1-C_6$ alkyl or is of the formula $N(R^7)(R^8)$, wherein $R^7$ and $R^8$ are independently hydrogen, $C_1-C_6$ haloalkyl, $C_1-C_6$ alkyl, $C_2-C_6$ alkenyl or together $R^7$ and $R^8$ form a pyrrolidine ring.

The term "substituted ... heteroaryl group" as used in the definition of Ar is intended to include heteroaryl groups, as defined above, having one or more substituents independently selected from the group consisting of halogen, $C_1-C_6$ alkyl, $C_1-C_6$ alkoxy, $C_2-C_6$ alkenyl, $C_2C_6$ alkynyl, $C_1-C_6$ alkylcarbamylthio, mercapto, $C_1-C_6$ haloalkyl, $C_1-C_6$ haloalkoxy, nitro, cyano, hydroxy, thiocyano, $(C_1-C_6)$ alkoxy $—(C_1-C_6)$ alkyl, $—S(O)_k—R^{10}$ or $—N(R^{11})(R^{12})$, wherein k, $R^{10}$, $R^{11}$ and $R^{12}$ have the meanings set forth above; and to include the N-oxides of heteroaryl groups.

One group of substituted hydroxybenzyl-pyrimidine preferred compounds is of the formula:

(III)

wherein

X, R, $R^1$, $R^2$, $R^3$, $R^4$ and $R^5$ have the same meanings as in formula (I);

$Y^1$, $Y^2$ and $Y^3$ are each independently hydrogen, halogen, $C_2-C_6$ alkenyl, $C_2-C_6$ alkynyl, $C_1-C_6$ alkyl, $C_1-C_6$ haloalkyl, $C_1-C_6$ alkoxy, $C_1-C_6$ haloalkoxy, nitro, cyano, $C_1-C_6$ alkylcarbamylthio, mercapto, hydroxy, thiocyano, $(C_1-C_6)$alkoxy-$(C_1-C_6)$alkyl, $—S(O)_k—R^{10}$ or $—N(R^{11})(R^{12})$, wherein k, $R^{10}$, $R^{11}$ and $R^{12}$ have the meanings set forth above; and n and m are each independently 0 or 1.

Another group of preferred compounds is substituted hydroxybenzyl-pyrazines of the formula:

(IV)

wherein X, R, $R^1$, $R^2$, $R^3$, $R^4$, $R^5$, $Y^1$, $Y^2$, $Y^3$, n and m have the same meanings as set forth with respect to formula (III).

Yet another group of preferred compounds is substituted hydroxybenzyl-substituted triazoles of the formula:

(V)

wherein

X, R, $R^1$, $R^2$, $R^3$, $R^4$ and $R^5$ have the same meaning as set forth above;

p is 0 or 1; and each Z is independently halogen, $C_1-C_6$ alkyl, $C_1-C_6$ haloalkyl, $C_1-C_6$ alkoxy, $C_1-C_6$ haloalkoxy, $C_1-C_6$ alkylcarbamylthio, $C_2-C_6$ alkenyl, $C_2-C_6$ alkynyl, mercapto, nitro, cyano, hydroxy, thiocyano, $(C_1-C_6)$ alkoxy-$(C_1-C_6)$alkyl, $—S(O)_k—R^{10}$ or $N(R^{11})(R^{12})$, wherein k, $R^{10}$, $R^{11}$ and $R^{12}$ have the same meaning as set forth above.

Still another group of preferred compounds is substituted hydroxybenzyl-imidazoles of the formula:

(VI)

wherein X, R, $R^1$, $R^2$, $R^3$, $R^4$, $R^5$ and Z have the same meaning as set forth above; and q is 0, 1 or 2.

Still a further group of preferred compounds is substituted hydroxybenzyl thiazoles of the formula:

(VII)

wherein X, R, $R^1$, $R^2$, $R^3$, $R^4$, $R^5$, Z and q have the same meaning as set forth above.

The formulae given above are intended to include tautomeric forms of the structures drawn therein, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intramolecular or inter-molecular hydrogen bonding, or otherwise.

The compounds of such formulae can exist in enantiomeric forms. The invention includes both individual enantiomers and mixtures of the two in all proportions.

As is employed herein, the term "hydrocarbyl", whether representing a substituent on its own or whether it is part of the definition of a larger group (e.g., as in hydrocarbyloxy, hydrocarbyl-$S(O)_k—$, etc.) is intended to include hydrocarbyl groups having from 1 to 12 carbon atoms. The term hydrocarbyl therefore includes, for example, $C_1$ to $C_{12}$ alkyl including both straight and branched chain isomers (e.g., methyl, ethyl, propyl, and hexyl); cycloalkyl of 3 to 12 carbon atoms (e.g., cyclopropyl, cyclobutyl and cyclohexyl); $C_2$ to $C_{12}$ alkenyl including for example allyl and crotyl; $C_2$ to $C_{12}$ alkynyl (e.g., propynyl); phenyl; phenylalkyl; alkylphenyl, alkenylphenyl, alkynylphenyl, alkylbenzyl, alkenylbenzyl, alkynyl benzyl, naphthyl and the like.

The term "substituted hydrocarbyl" is intended to include hydrocarbyl groups, as defined above, having one or more substituents selected from the group consisting of halogen (i.e., fluorine, chlorine, bromine, and iodine); $C_{1-4}$ alkoxy; $C_{1-4}$ alkyl-$S(O)_k—$; nitro; cyano; carboxy, and salts, amides and esters thereof; alkanoyl of 2 to 4 carbon atoms; and phenyl optionally substituted by one or more $C_{1-4}$ alkyl, $C_{1-4}$ alkoxy, $C_{1-4}$ alkyl-$S(O)_k—$, nitro, fluorine, chlorine, bromine, cyano, or $CF_3$ groups. In the above definitions, k is 0, 1 or 2.

Further, when the hydrocarbyl radical is a substituted aryl radical (e.g., phenyl, benzyl or naphthyl), the substituents may include one or more of the substituents listed in the last foregoing paragraph.

The expression "salts, amides, and esters thereof" used above in relation to carboxy substitution includes, for example, salts formed from alkali metal (e.g., sodium, potassium, and lithium), alkaline earth metals (e.g., calcium and magnesium), the ammonium ion, and substituted ammonium ions wherein one, two, three, or four of the hydrogen atoms have been replaced by optionally substituted $C_{1-6}$ hydrocarbyl moieties as defined above.

Further, in the above definitions the term "halogen" includes fluoro, chloro, bromo and iodo groups. In polyhalogenated groups the halogens may be the same or different.

Particularly preferred compounds include:

2-(1-N-allylcarbamyloxy-2'-trifluoromethylbenzyl) pyrazine;
2-(1-N-t-butylcarbamyloxy-2'-trifluoromethylbenzyl) pyrazine;
2-[1-(1-pyrrolidinyl)carbonyloxy-2'-trifluoromethylbenzyl] pyrazine;
2-(1-N-ethylcarbamyloxy-2'-methylbenzyl)pyrazine;
2-(1-N-ethylcarbamyloxy-2'-chlorobenzyl)pyrazine;
2-(1-N,N-dimethylcarbamyloxy-2'-methylbenzyl)pyrazine;
2-(1-N,N-dimethylcarbamyloxy-2'-chlorobenzyl)pyrazine;
1N-oxide of 2-(1-N-ethylcarbamyloxy-2'-chlorobenzyl) pyrazine;
2-(1-N-allylcarbamyloxy-2'-chlorobenzyl)pyrazine;
2-(1-N-allylcarbamyloxy-2'-methylbenzyl)pyrazine;
2-(1-N,N-dimethylcarbamyloxy-2'-ethylbenzyl)pyrazine;
2-(1-N-methylcarbamyloxy-2'-ethylbenzyl)pyrazine;
2-(1-N-ethylcarbamyloxy-2'-ethylbenzyl)pyrazine;
2-(1-N-allylcarbamyloxy-2'-ethylbenzyl)pyrazine;
2-(1-t-butylcarbonyloxy-2'-ethylbenzyl)pyrazine;
2-(1-N-ethylcarbamyloxy-2'-fluoro-5'-chlorobenzyl) pyrazine;
2-(1-N-allylcarbamyloxy-2'-fluoro-5'-chlorobenzyl) pyrazine;
2-(1-N-allylcarbamyloxy-2'-iodobenzyl)pyrazine;
2-(1-N-ethylcarbamyloxy-2'-iodobenzyl)pyrazine;
2-[1-N-(2-chloroethyl)carbamyloxy-2'-trifluoromethylbenzyl]pyrazine;
2-(1-N-propylcarbamyloxy-2'-ethylbenzyl)pyrazine;
1N-oxide of 2-(1-N-ethylcarbamyloxy-2'-trifluoromethylbenzyl)pyrazine;
5-(1-hydroxy-2'-trifluoromethylbenzyl)pyrimidine;
5-(1-N-ethylcarbamyloxy-2'-trifluoromethylbenzyl) pyrimidine;
5-(1-trimethylacetoxy-2'-trifluoromethylbenzyl)pyrimidine;
4-chloro-5-(1-N,N-dimethylcarbamyloxy-2'-methylbenzyl) pyrimidine;
4-methoxy-5-(1-N,N-dimethylcarbamyloxy-2'-trifluoromethylbenzyl)pyrimidine;
4-methyl-5-(1-N,N-dimethylcarbamyloxy-2'-trifluoromethylbenzyl)pyrimidine;
4-ethyl-5-(1-N,N-dimethylcarbamyloxy-2'-trifluoromethylbenzyl)-pyrimidine;
4-methoxy-5-(1-t-butylcarbonyloxy-2'-trifluoromethylbenzyl)pyrimidine;
4-ethyl-5-(1-t-butylcarbonyloxy-2'-trifluoromethylbenzyl) pyrimidine;
4-methyl-5-(1-t-butylcarbonyloxy-2'-trifluoromethylbenzyl)pyrimidine;
4-methyl-5-(1-N-ethylcarbamyloxy-2'-trifluoromethylbenzyl)pyrimidine;
4-ethyl-5-(1-N-ethylcarbamyloxy-2'-trifluoromethylbenzyl) pyrimidine;
4-ethyl-5-(1-N-methylcarbamyloxy-2'-trifluoromethylbenzyl)pyrimidine; and
N-(1-N,N-dimethylcarbamyloxy-2'-methoxy-5'-bromobenzyl)imidazole.

The compounds of the present invention have been found to be active herbicides, possessing utility as pre-emergence and post-emergence herbicides and useful against a wide range of plant species including broadleaf, grassy and perennial species.

This invention therefore also relates to a method for controlling undesirable vegetation comprising applying to a locus where control of such vegetation is desired, either prior or subsequent to the emergence of such vegetation, a herbicidally effective amount of a compound as described herein, together with an inert diluent or carrier suitable for use with herbicides.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions.

The term "agriculturally acceptable salt" is easily determined by one of ordinary skill in the art and includes hydrohalogen, acetic, sulfonic, phosphonic, inorganic and organic acid salts.

In general, the compounds of this invention are prepared by (A) reacting a substituted or unsubstituted 5- or 6-membered heteroaryl compound having 2 or 3 ring nitrogen atoms or a 5-membered heteroaryl compound having two ring heteroatoms, one of which is nitrogen and the other being sulfurn or oxygen (the remainder of the ring atoms being carbon), with a substituted benzaldehyde of the formula:

$$\begin{array}{c} CHO \\ R^5 \diagup\diagdown R^1 \\ | \phantom{xxx} | \\ R^4 \diagdown\diagup R^2 \\ R^3 \end{array}$$

wherein $R^1$, $R^2$, $R^3$, $R^4$ and $R^5$ are as defined for formula (I) above in the presence of a suitable base to form a substituted hydroxybenzyl-nitrogen-containing heteroaryl compound of formula (II) above; and, where appropriate, (B) reacting such substituted hydroxybenzyl heteroaryl compound with an appropriate derivatizing agent (e.g., an alkyl or aryl acid halide, carbamoyl halide, alkyl halide, sulfonyl halide, phosphoryl halide or trialkylsilyl halide) or an appropriate isocyanate, or sequentially first with phosgene or a phosgene equivalent and then with an appropriate amine, to produce the desired compound.

Typically, about 1–2 equivalents of an appropriate base (such as lithium diisopropylamide or n-butyl lithium) and a substituted or unsubstituted heteroaryl compound, as defined above, in a solvent (such as ethylene glycol dimethyl ether, tetrahydrofuran, diethyl ether or the like) are combined at a temperature of between about −100° and about 0° C. After suitable blending, about 1–2 equivalents of the substituted benzaldehyde are generally added.

This reaction mixture is typically agitated and slowly warmed up to ambient temperature (about 25° C.) over a period of 1–24 hours. The reaction may be quenched with an aqueous solution and the substituted hydroxybenzyl heteroaryl compound so produced may be recovered by conventional techniques (such as extraction, filtration and the like) and purified by known methods, e.g., flash chromatography.

In the second step, the substituted hydroxybenzyl heteroaryl compound of formula (II), in a suitable solvent (such as tetrahydrofuran, methylene chloride, or the like) may typically be added to between about 1 and about 4 equivalents of an appropriate base (such as sodium hydride or triethylamine) at about 0° C. Between about 1 and about 3 equivalents of derivatizing agent (such as a carbamoyl halide, an alkyl halide, a sulfonyl halide or a phosphosphoryl halide, or an alkyl or aryl acid halide, or a trialkylsilyl halide) is then added and the mixture agitated until the reaction is complete. The reaction may be quenched by the addition of an aqueous solution, and the products recovered by conventional techniques, such as extraction, filtration and the like. The product so recovered may then be purified by conventional techniques such as flash chromatography or the like.

Alternatively, in the second step, the substituted hydroxybenzyl heteroaryl compound in suitable solvent (such as tetrahydrofuran, methylene chloride or the like) may be added to between about 2 and about 3 equivalents of an appropriate isocyanate. Between about 1 and about 100 mole percent of one or more appropriate catalysts, e.g., triethyl amine or dibutyl tin dilaurate, may be added and the reaction mixture agitated at between about 0° and 100° C. for an appropriate period (e.g., 2 to 24 hours). The product may be recovered by conventional techniques (such as extraction, filtration or the like) and may be purified by conventional techniques such as flash chromatography or the like.

In cases where the Ar moiety of the inventive compounds is a pyrimidine group having an alkyl substituent at the 4-position, the compounds are made by the following general procedure. First, a benzoyl chloride is reacted with the magnesium enolate of an appropriate beta-ketoester to form a triketo intermediate followed by hydrolysis and decarboxylation to a beta diketone intermediate. The diketone is then converted to the alkoxy methylene or dialkylaminomethylene beta diketone by standard methods. Final ring closure to the pyrimidine is accomplished by heating with formamidine acetate in an alcoholic solvent, followed by reduction of the resulting benzoyl pyrimidine, to produce a hydroxybenzyl pyrimidine compound within the scope of formula (II). Derivatives of these hydroxybenzyl pyrimidine compounds are produced according to the general procedures for the second step described above.

The herbicidal compositions of this invention comprise a compound of formula (I) above and a suitable carrier, which carriers are well known to one of ordinary skill in the art.

The compounds of the present invention are useful as herbicides and can be applied in a variety of ways known to those skilled in the art, at various concentrations. The compounds are useful in controlling the growth of undesirable vegetation by pre-emergence or post-emergence application to the locus where control is desired. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as amount 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants etc.). The formulations can also be prepared by a tank mix method, in which the ingredients are obtained separately and combined at the grower site.

The compounds of the present invention are also useful when combined with other herbicides and/or defoliants, desiccants, growth inhibitors, and the like. These other materials can comprise from about 5% to about 95% of the active ingredients in the formulations. These combinations frequently provided a higher level of effectiveness in controlling weeds and often provide results unattainable with separate formulations of the individual herbicides.

Examples of other herbicides, defoliants, desiccants and plant growth inhibitors with which the compounds of this invention can be combined are:

A. benzo-2,1,3-thiadiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 4-benzoylpyrazole derivatives such as pyrazoxyfen, pyrazolate and benzofenap;

D. dinitrophenols and their derivatives (e.g. acetates such as DNOC, dinoterb, dinoseb, and its ester dinoseb acetate;

E. dinitroaniline herbicides such as dinitramine, trifluralin, ethalfluralin, pendimethalin and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba, and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil, and ioxynil;

Q. haloalkanoic herbicides such as dalapon, TCA and salts thereof;

R. diphenylether herbicides such as lactofen, flurogly-cofen or salts or esters thereof, nitrofen, bifenox, acifluorfen and salts and esters thereof, oxyfluorfen and fomesafen, chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. triketone and cyclohexanedione herbicides such as alloxydim, sulcotrione and salts thereof, sethoxydim, cycloxydim, tralkoxydim, and clethodim;

U. sulfonyl urea herbicides such as chlorosulfuron, sulfometuron, metsulfuron and esters thereof, benzsulfuron and esters thereof such as the ester thereof methyl, DPX-M6313, chlorimuron and esters such as the ethyl ester thereof, pirimisulfuron and esters such as the methyl ester thereof, DPX-LS300, and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, and diflufenican;

X. amino acid herbicides such as glyphosate and glufosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;

BB. examples of useful contact herbicides include bipyridylium herbicides such as those in which the active entity is paraquat and those in which the active entity is diquat.

*These compounds are preferably employed in combination with a safener such as 2,2-dichloro-N,N-di-2-propenylacetamide (dichlormid).

These formulations can be applied to the areas where control is desired by conventional methods. Dust and liquid compositions, for example, can be applied by the use of power-dusters, boom and hand sprayers, and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.

5% dust:
 5 parts active compound
 95 parts talc

2% dust:
 2 parts active compound
 1 part highly dispersed silicic acid
 97 parts talc These dusts are formed by mixing the components then grinding the mixture to the desired particle size.

5% granules:
 5 parts active compound
 0.25 part epichlorohydrin
 0.25 part cetyl polyglycol ether
 3.5 parts polyethylene glycol
 91 part kaolin (particle size 0.3–0.8 mm)

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

Wettable powders:
70%:
 70 parts active compound
 5 parts sodium dibutylnaphthylsulfonate
 3 parts naphthalenesulfonic acid/phenolsulfonic acid/ formaldehyde condensate (3:2:1)
 10 parts kaolin
 12 parts Champagne chalk 40%:
 40 parts active compound
 5 parts sodium lignin sulfonate
 1 part sodium dibutylnaphthalene sulfonic acid
 54 parts silicic acid 25%:
 25 parts active compound
 4.5 parts calcium lignin sulfate
 1.9 parts Champagne chalk/hydroxyethyl cellulose (1:1)
 1.5 parts sodium dibutylnaphthalene sulfonate
 19.5 silicic acid
 19.5 parts Champagne chalk
 28.1 parts kaolin 25%:
 25 parts active compound
 2.5 parts isooctylphenoxy-polyethylene-ethanol
 1.7 parts Champagne chalk/hydroxyethyl cellulose (1:1)
 8.3 parts sodium aluminum silicate
 16.5 parts kieselguhr
 46 parts kaolin 10%:
 10 parts active compound
 3 parts of a mixture of sodium salts of saturated fatty alcohol sulfates
 5 parts naphthalenesulfonic acid/formaldehyde condensate
 82 parts kaolin These wettable powders are prepared by intimately mixing the active compounds with the additives in suitable mixers and grinding the resulting mixture in mills or rollers.

Emulsifiable concentrate:
25%:
 25 parts active substance
 2.5 parts epoxidized vegetable oil
 10 parts of an alkylarylsulfonate/fatty alcohol polyglycol ether mixture
 5 parts dimethylformamide
 57.5 parts xylene The amount of the present compositions which constitute a herbicidally effective amount depends upon the nature of the seeds or plants to be controlled. The rate of application of active ingredients varies from about 0.01 to about 25 pounds per acre, preferably about 0.10 to about 10 pounds per acre with the actual amount depending on the overall costs and the desired results. It will be readily apparent to one skilled in the art that compositions exhibiting lower herbicidal activity will require a higher dosage than more active compounds for the same degree of control.

EXAMPLES

The following examples are intended to illustrate further the present invention and are not intended to limit the scope of this invention in any manner whatsoever. The structures were confirmed by NMR, IR and/or mass spectra. All reactions were run under an inert atmosphere.

Example 1

Preparation of 2-(1-N-ethylcarbamyloxy-2'-trifluoromethylbenzyl)-pyrazine (Compound No. 3)

(A) To a 500 ml round bottom flask equipped with a magnetic stirrer, 26.2 ml of 2,2,6,6-tetramethylpiperidine (TMP) and 150 ml tetrahydrofuran (THF) were added and then cooled to −70° C. 65 ml of a 2.5M solution of n-butyl lithium in hexane were then added over a period of 30 minutes. The resulting solution was allowed to warm up to 5° C., kept at 0°±5° C. for 30 minutes, and then cooled to −70° C. 9.6 g of pyrazine in 50 ml THF were then added over a period of one hour, while maintaining the temperature at between −65° and −70° C. to produce a dark brown mixture. The reaction mixture was then stirred at −70° C. for 45 minutes. 17.4 ml of 2-trifluorobenzaldehyde were then added over a period of 30 minutes at −70° C. The resulting dark brown reaction mixture was stirred at −70° C. for 90 minutes. A mixture of 55 ml concentrated HCl, 55 ml ethanol and 100 ml THF was then added to the reaction mixture over a period of 30 minutes, while keeping the temperature below −60° C. The reaction mixture was allowed to warm slowly to room temperature and stirred overnight.

The solvent was stripped from the reaction mixture, leaving a dark brown residue. This residue was extracted with water and methylene chloride. The methylene chloride layer was washed with water, dried (MgSO$_4$), filtered and stripped to a solid. The solid was rinsed with hexane with a small amount of methylene chloride to yield 8.28 g of 2-(1-hydroxy-2'-trifluoromethylbenzyl)-pyrazine (Compound No. 34).

(B) One gram of 2-(1-hydroxy-2'-trifluoromethylbenzyl) pyrazine was dissolved in 20 ml of methylene chloride to produce a brownish solution. 0.65 ml of ethyl isocyanate were added at room temperature followed by 5 drops of triethylamine (TEA) and 2 drops of dibutyl tin dilaurate (DBTDL). The reaction mixture was stirred at room temperature overnight. The solvent was then stripped from the reaction mixture to yield 1.4 grams of 2-(1-N-ethylcarbamyloxy-2'-trifluoromethylbenzyl)pyrazine in the form of a brown oil.

Example 2

Preparation of 2-(1-trimethylacetoxy-2'-methoxy-5'-bromobenzyl)-pyrazine (Compound No. 32)

(A) To a 500 ml round bottom flask equipped with a magnetic stirrer, 14 ml of TMP and 60 ml THF were added and then cooled to −70° C. 35 ml of a 2.5M solution of n-butyl lithium in hexane were then added over a period of 30 minutes. The resulting solution was allowed to warm up to 5° C., kept at 0°±5° C. for 30 minutes, and then cooled to −70° C. 50 g of pyrazine in 35 ml THF were then added over a period of one hour, while maintaining the temperature at between −65° and −70° C. to produce a dark brown mixture. The reaction mixture was then stirred at −70° C. for 45 minutes. 14 g of 2-methoxy-5-bromobenzaldehyde were then added over a period of 30 minutes at −70° C. The resulting reaction mixture was stirred at −70° C. for 90 minutes. A mixture of 28 ml concentrated HCl, 28 ml ethanol and 28 ml THF was then added to the reaction mixture over a period of 30 minutes, while keeping the temperature below −60° C. The reaction mixture was stirred in a dry ice bath until the dry ice melted, and then left at room temperature overnight.

The solvent was stripped from the reaction mixture, and the residue was extracted with water and methylene chloride. The methylene chloride layer was washed with water, dried (MgSO$_4$), filtered and stripped to a solid. The solid was rinsed with hexane with a small amount of methylene chloride to yield 2.0 g of 2-(1-hydroxy-2'-methoxy-5'-bromobenzyl)pyrazine.

(B) 0.6 g of 2-(1-hydroxy-2'methoxy-5'-bromobenzyl) pyrazine were dissolved in 15 ml of methylene chloride. At 0° C., 0.2 g of NaH were added, resulting in the evolution of a gas and formation of a precipitate. 0.4 ml of trimethylacetyl chloride were added in one portion. The reaction mixture was stirred at room temperature overnight. The solvent was then stripped from the reaction mixture, and the residue was extracted with ice water and methylene chloride. The methylene chloride layer was washed with water, dried (MgSO$_4$), filtered and stripped of the solvent to yield 0.9 g of 3-(1-trimethylacetoxy-2'-methoxy-5'-bromobenzyl)-pyrazine.

Example 3

Preparation of 2-(1-N,N-dimethylcarbomyloxy-2'-methylbenzyl)-pyrazine (Compound No. 11)

(A) To a 500 ml round bottom flask equipped with a magnetic stirrer, 14 ml of TMP and 50 ml THF were added and then cooled to −70° C. 35 ml of a 2.5M solution of n-butyl lithium in hexane were then added over a period of 10 minutes while maintaining the temperature below −70° C., resulting in the formation of a white precipitate. After stirring at −70° C. for 10 minutes, the reaction mixture was allowed to warm up to 0° C. and kept at 0° C. for 10 minutes. The reaction mixture turned to a clear yellow solution which was then cooled to −70° C. again. A solution of 5.0 g of pyrazine in 25 ml THF was then added over a period of 15 to 20 minutes, while maintaining the temperature at below −60° C., which produced a dark brown solution. The reaction mixture was then stirred at −70° C. for one hour. 8.0 ml of 2-methylbenzaldehyde were then added, while the temperature was kept below −60° C. The resulting dark brown reaction mixture was stirred at −70° C. for about 2 hours. A solvent mixture of 28 ml concentrated HCl, 28 ml ethanol and 28 ml THF was then added to the reaction mixture slowly at −70° C. The dark brown reaction mixture was stirred in a dry ice bath until the dry ice melted, and then left at room temperature overnight.

The reaction mixture was extracted with methylene chloride and the methylene chloride layer was decolorized with charcoal, filtered through dicalite and silica gel to produce a bright orange solution. The solvent was stripped and the oil residue was triturated with hexane and filtered to yield 6.2 g of solid 2-(1-hydroxy-2'-methylbenzyl)-pyrazine (Compound No. 35).

(B) 0.7 g of 2-(1-hydroxy-2'-methylbenzyl)-pyrazine were dissolved in 20 ml of THF and cooled to 0° C. 0.3 g of NaH were added, resulting in the evolution of a gas and formation of a precipitate. After stirring the resulting brown reaction mixture for 10 minutes, 0.5 ml of N,N-dimethylcarbamyl chloride were added all at once. The reaction mixture was stirred at room temperature overnight. The reaction mixture was then worked up by extraction with ice water and methylene chloride. The methylene chloride layer was washed with water, then washed with brine, dried (MgSO$_4$), filtered and then stripped to an oil which solidified upon standing. The solid was filtered off and rinsed with hexane to yield 0.78 g of solid 2-(1-N,N-dimethylcarbamyloxy-2'-methylbenzyl)-pyrazine.

Example 4

Preparation of the 1N-oxide of 2-(1-N-ethylcarbamyloxy-2'-chlorobenzyl)-pyrazine (Compound No. 13)

(A) Substantially the same procedure as in Example 3(A) was followed, with the exception that 8.0 ml of 2-chlorobenzaldehyde were used instead of the 8.0 ml of 2-methylbenzaldehyde. After stripping the solvent from the reaction mixture, a yellowish residue was formed. The yellowish residue was put onto a silica gel column and eluted with a 1:1 mixture of hexane and diethyl ether to yield 8.08 g of 2-(1-hydroxy-2'-chlorobenzyl)-pyrazine (Compound No. 36).

(B) 1.8 g of 2-(1-hydroxy-2'-chlorobenzyl)-pyrazine were dissolved in 25 ml of methylene chloride. 1.3 ml of ethyl isocyanate were added in one portion, followed by 5 drops of TEA and 2 drops of DBTDL. The reaction mixture was then stirred at room temperature overnight. The solvent was then stripped and the remaining brown oil residue was crystallized from diethyl ether and hexane. The solid was recovered by filtration, yielding 2.19 g of solid 2-(1-N-ethylcarbamyloxy-2'-chlorobenzyl)-pyrazine.

(C) 1.19 g of 2-(1-N-ethylcarbamyloxy-2'-chlorobenzyl)-pyrazine were dissolved in 45 ml of methylene chloride. 0.86 ml of peracetic acid were then added and the reaction mixture was stirred overnight. The reaction mixture was then worked up with water and methylene chloride. The methylene chloride layer was washed with brine, dried (MgSO$_4$), filtered and stripped to a residue. The residue was purified on a silica gel column and eluted with a 1:1 mixture of hexane: ethyl acetate, followed by elution with 100% ethyl acetate, to yield 0.5 g of the 1N-oxide of 2-(1-N-ethylcarbamyloxy-2'-chlorobenzyl)-pyrazine.

Example 5

Preparation of 2-(1-N-ethylcarbamyloxy-2'-trifluoromethylbenzyl)-pyrazine (Compound No. 26)

(A) 2-(1-hydroxy-2'-trifluoromethylbenzyl)-pyrazine was produced according to the procedure described in Example 1(A).

(B) 1.0 g of 2-(1-hydroxy-2'-trifluoromethylbenzyl)-pyrazine was dissolved in 20 ml of methylene chloride. 0.7 ml of 2-chloroethylisocyanate were added, followed by 2 drops of DBTDL and 5 drops of TEA. The reaction mixture was then stirred overnight at room temperature. The solvent was then stripped from the reaction mixture and the resulting brown oil was put onto a silica gel column and eluted with a 1:1 mixture of hexane and diethyl ether to yield 1.2 g of 2-(1-N-ethylcarbamyloxy-2'-trifluoromethylbenzyl)-pyrazine in the form of an oil.

Example 6

Preparation of 2-(1-N-allylcarbamyloxy-2'-fluoro-5'-chlorobenzyl)-pyrazine (Compound No. 23)

(A) 35 ml of a 2.5M solution of butyl lithium were added to 14 ml of TMP in 35 ml THF over a period of 10 minutes at a temperature of −70° C. After stirring at −70° C. for 10 minutes, the reaction mixture was allowed to warm up to 0° C. and kept at 0° C. for 10 minutes. The reaction mixture was then cooled to −70° C. again and a solution of 5.0 g of pyrazine in 25 ml THF was then added over a period of 15–20 minutes, while maintaining the temperature below −60° C. The reaction mixture was then stirred at −70° C. for one hour. 10.4 g of 2-fluoro-6-chlorobenzaldehyde were added, while keeping the temperature below −60° C. and the resulting reaction mixture was then stirred at −70° C. for about two hours. The reaction mixture was allowed to warm slowly to room temperature and stirred overnight. 45 ml of saturated $NH_4Cl$ were added to the reaction mixture. Then, 150 ml of methylene chloride were added and the layers were separated. The methylene chloride layer was washed with brine, dried ($MgSO_4$), filtered and stripped to a dark brown residue. The residue was put on a silica gel column and eluted with a 4:1 mixture of hexane:diethyl ether, then 2:1 hexane:diethyl ether. The desired fraction yielded 2.0 g of 2-(1-hydroxy-2'-fluoro-6'-chlorobenzyl)pyrazine in a yellow, semi-solid form.

(B) 0.56 g of 2-(1-hydroxy-2'-fluoro-6'-chlorobenzyl)-pyrazine were dissolved in 20 ml of methylene chloride. 0.45 ml of N-allylisocyanate were added, followed by 2 drops of DBTDL and 5 drops of TEA. The reaction mixture was then stirred overnight at room temperature. The solvent was stripped from the reaction mixture which was then put onto a silica gel column and eluted with a 1:1 mixture of hexane and diethyl ether to yield 0.8 g of 2-(1-N-allylcarbamyloxy-2'-fluoro-6'-chlorobenzyl)-pyrazine.

Example 7

Preparation of 5-(1-hydroxy-2'-trifluoromethylbenzyl)-pyrimidine (Compound No. 37)

To a suspension of 7.0 g of 5-bromopyrimidine in 150 ml of diethyl ether at −75° C., 20 ml of 2.5M butyl lithium in hexane were added while keeping the temperature below −50° C. The reaction mixture was then stirred at −75° C. for 1.5 hours. 7.66 g of 2-trifluoromethylbenzaldehyde were added while keeping the temperature below −50° C. and the reaction mixture was then stirred at −75° C. for one hour. The reaction mixture was then quenched with water. The resulting layers were separated. The aqueous layer was extracted again with diethyl ether. The combined organic layers were dried ($MgSO_4$), filtered and concentrated to a yellow oil which turned orange upon standing overnight. Purification by column chromatography (silica gel), eluted first with a 1:1 mixture of hexane and diethyl ether, and then with diethyl ether, to yield 0.13 g of 5-(1-hydroxy-2,-trifluoromethylbenzyl)pyrimidine.

Example 8

Preparation of 5-(1-N-ethylcarbamyloxy-2'-trifluoromethylbenzyl)-pyrimidine (Compound No. 38)

The 5-(1-hydroxy-2'-trifluoromethylbenzyl)pyrimidine (0.5 g) produced according to Example 7 was dissolved in 30 ml of methylene chloride. Ethyl isocyanate (0.2 g) was added at room temperature followed by 10 drops of TEA and 5 drops of DBTDL. The reaction mixture was stirred at room temperature overnight. After stripping the solvent, the reaction mixture was put onto a silica gel column and eluted with a 1:1 mixture of diethyl ether and methylene chloride to yield 0.55 g of 5-(1-N-ethylcarbamyloxy-2'-trifluoromethylbenzyl)-pyrimidine in the form of an oil.

Example 9

Preparation of 5-(1-trimethylacetoxy-2'-trifluoromethylbenzyl)-pyrimidine (Compound No. 39)

To a solution of 0.5 g of 5-(1-hydroxy-2'-trifluoromethylbenzyl)-pyrimidine (produced according to Example 7) in 15 ml THF at room temperature, 0.2 g of NaH (80%) were added. Gas evolution was observed. After 30 minutes, 0.4 g of trimethylacetyl chloride were added to the reaction mixture and gas evolution was again observed. After 3 hours of stirring, the reaction mixture was worked up with water and the organic materials extracted with diethyl ether. The organic layer was dried ($MgSO_4$), filtered and concentrated to a yellow oil. Elution on a silica gel column with a 1:1 mixture of diethyl ether and hexane yielded 0.56 g of 5-(1-trimethylacetoxy-2'-trifluoromethylbenzyl)-pyrimidine.

Example 10

Preparation of 4-methoxy-5-(1-N,N-dimethylcarbamyloxy-2'-trifluoromethylbenzyl)-pyrimidine (Compound No. 48)

2-chloro-4-methoxy-5-(1-N,N-dimethylcarbamyloxy-2'-trifluoromethylbenzyl)pyrimidine (Compound No. 47) was produced by metallation of the known compound 2-chloro-4-methoxypyrimidine with lithium TMP and reaction with 2-trifluorobenzaldehyde (according to a process analogous to Example 1(A)), followed by reaction of the resulting hydroxybenzyl pyrimidine with N,N-dimethylcarbamyl chloride (according to a process analogous to Example 3(B)).

To a solution of 2-chloro-4-methoxy-5-(1-N,N-dimethylcarbamyloxy-2'-trifluoromethylbenzyl)-pyrimidine in 8 ml of methanol were added 100 mg of 5% Pd on carbon. A total of 20 hours shaking on a Parr Apparatus under 50 psi of hydrogen, plus the addition of another 80 mg of 5% Pd on carbon was required for completion of the reaction. The mixture was suction filtered through dicalite and evaporated to yield 1.06 g of a yellow solid. Purification of the crude product was accomplished by chromatography on silica gel with dichloromethane-methanol (95:5) as eluant to yield 0.62 g of 4-methoxy-5-(1-N,N-dimethyl-carbamyloxy-2'-trifluoromethylbenzyl)pyrimidine as a viscous yellow oil.

Example 11

Preparation of 4-ethyl-5-(1-N,N-dimethylcarbamyloxy-2'-trifluoromethylbenzyl)-pyrimidine (Compound No. 62)

To 17.25 g of ethyl 3-oxo-pentanoate in 150 ml THF were added 13.6 g of magnesium ethoxide. The solution was refluxed for 3 hours. The THF was evaporated in vacuo along with residual ethanol. To the viscous yellow oil dissolved in a chilled solution of 50 ml THF, 2-(trifluoromethyl)benzoyl chloride was added dropwise over 30 minutes. The yellow mixture was stirred at room temperature for 1 hour, then at reflux for 4 hours. The solvent was evaporated in vacuo and the residue partitioned between ether and 2N HCl. The combined organic layers were washed with saturated sodium chloride, dried (MgSO$_4$), filtered and evaporated to yield 38.3 g of ethyl 3-oxo-[2-(2-trifluoromethyl)benzoyl]-pentanoate as a mobile oil.

A solution of 5.0 g of ethyl 3-oxo-[2-(2-trifluoromethyl)benzoyl]-pentanoate in 40 ml of 48% hydrobromic acid was heated to reflux for 4 hours. The aqueous solution was extracted three times with 25 ml of methylene chloride. The organic layers were combined, dried (MgSO$_4$) and concentrated in vacuo to produce 3.01 g of 1-[(2-trifluoromethyl)phenyl]-1,3-pentanedione as a mobile oil. The material was further purified via a bulb-to-bulb distillation at 0.005 mm Hg to yield 1.6 g of 1-[2-trifluoromethyl)phenyl]-1,3-pentanedione as a clear, colorless mobile oil.

A solution of 5.0 g of 1-[(2-trifluoromethyl)phenyl]-1,3-pentanedione and 2.6 g of dimethylformamide dimethylacetal was stirred overnight. The volatiles were removed by bulb-to-bulb distillation at 80° C. and 0.01 mm Hg to leave 5.75 g of a viscous oil of 1-[(2-trifluoromethyl)phenyl-2-[(dimethylamino)methylene]-1,3-pentanedione.

To a solution of 318 mg of 1-[(2-trifluoromethyl)phenyl]-2-[(dimethylamino)methylene]-1,3-pentanedione and 243 mg of formamidine acetate in 2.5 ml ethanol were added 0.63 ml of 25% sodium methoxide in methanol. After refluxing the solution for 1.5 hours, the mixture was allowed to cool before removal of the solvent in vacuo. The residue was partitioned between 25 ml methylene chloride and 25 ml water. The organic layer was dried (MgSO$_4$) and concentrated in vacuo to yield 241 mg of 4-ethyl-5-[(2-trifluoromethyl)benzoyl]-pyrimidine as a viscous oil.

To a solution of 4-ethyl-5-[(2-trifluoromethyl)benzoyl]-pyrimidine in 2 ml of ethanol were added 23 mg of sodium borohydride. After stirring for 1 hour at room temperature, the mixture was concentrated in vacuo. Three ml of water were added which was then made acidic by the addition of 3N hydrochloric acid. The mixture was neutralized with sodium bicarbonate and the aqueous solution extracted three times with 3.5 ml methylene chloride. The organic layers were combined, dried (MgSO$_4$) and concentrated in vacuo to yield 199 mg of 4-ethyl-5-(1-hydroxy-2'-trifluoromethylbenzyl)-pyrimidine (Compound No. 59) as a viscous orange oil.

To an oil free suspension of sodium hydride and dimethylcarbamyl chloride in 2 ml of THF at room temperature was added dropwise a solution of 460 mg of 4-ethyl-5-(1-hydroxy-2'-trifluoromethylbenzyl)-pyrimidine in 2 ml THF. After 45 minutes, the reaction mixture was combined with 25 ml of ether and this solution was washed first with water and then with saturated sodium chloride. The organic layer was dried (MgSO$_4$) and concentrated in vacuo to yield 596 mg of a viscous oil. This material was purified via chromatography on silica gel using hexane-ethylacetate (3:1) as the eluant to afford 260 mg of 4-ethyl-5-(1-N,N-dimethylcarbamyloxy-2'-trifluoromethylbenzyl)-pyrimidine as a yellow oil.

Example 12

Preparation of N-(1-trimethylacetoxy-2'-trifluoromethylbenzyl)-imidazole (Compound No. 64)

To a solution of 1.5 g of imidazole in 30 ml of THF at 0° C., 8.8 ml of a 2.5M solution of n-butyl lithium in hexane were added slowly over about 7 minutes. The reaction mixture became light yellow and cloudy. After 1.5 hours, 4.2 g of 2-trifluoromethylbenzaldehyde were added slowly at about 10° C. The reaction mixture was allowed to warm to room temperature and then stirred at room temperature over the weekend. 2.9 g of trimethylacetyl chloride were added slowly at room temperature and the mixture was stirred over the weekend. Ice was added to quench the reaction and the layers were separated. The organic layer was dried (MgSO$_4$), filtered and concentrated. The residue was put onto a silica gel column and eluted with a 1:1 mixture of hexane:ethyl acetate to yield 1.5 g of N-(1-trimethylacetoxy-2'-trifluoromethylbenzyl)-imidazole in the form of a clear oil.

Example 13

Preparation of N-(1-N,N-dimethylcarbamyloxy-2'-trifluoromethylbenzyl)-imidazole (Compound No. 65)

To a solution of 1.5 g of imidazole in 50 ml of THF at 0° C., 8.8 ml of a 2.5M solution of n-butyl lithium in hexane were slowly added. At the end point, the color changed to bright yellow and after 5 minutes a precipitate formed. 4.2 g of 2-trifluoromethylbenzaldehyde were added slowly at room temperature and the reaction mixture were stirred overnight. 2.6 g of N,N-dimethylcarbamylchloride was added slowly and the reaction mixture was stirred over the weekend at room temperature. Hexanes (50 ml) were added and solid from the resulting reaction mixture was collected by suction filtration. The solid was washed with hexanes (50 ml). The filtrate was dried, filtered, concentrated and purified on a silica gel column (eluted with 100% ethyl acetate). The solid was dissolved in water and organic materials were extracted into ethyl acetate. The organic layer was dried (MgSO$_4$), filtered, and concentrated. The resulting oil, which solidified upon standing, yielded 0.17 g of N-(1-N,N-dimethylcarbamyloxy-2'-trifluoromethylbenzyl)-imidazole. The total yield of N-(1-N,N-dimethylcarbamyloxy-2'-trifluoromethylbenzyl)-imidazole from the filtrate and solid was 0.55 g.

Example 14

Preparation of N-(1-N,N-dimethylcarbamyloxy-2'-methoxy-5'-bromobenzyl)-imidazole (Compound No. 66)

To a solution of 1.5 g of imidazole in 25 ml of THF at 0° C., 8.8 ml of a 2.5M solution of n-butyl lithium in hexane were added slowly. At the end point, the reaction mixture turned yellow. 4.73 g of 2-methoxy-5-bromobenzaldehyde were added in one portion and the reaction mixture was allowed to warm to room temperature and stirred overnight. 2.6 g of N,N-dimethylcarbamylchloride were added slowly at room temperature and the reaction mixture was stirred for 5 days. Ice water was added and then the reaction mixture was partitioned between ethyl acetate and water. The layers were separated and the organic layer was dried (MgSO$_4$), filtered and adsorbed onto a silica gel column. Elution with a 1:1 mixture of hexane and ethyl acetate followed by 100% ethyl acetate yielded 0.36 g of N-(1-N,N-dimethylcarbamyloxy-2'-methoxy-5'-benzyl)-imidazole in the form of an off-white solid.

Example 15

Preparation of N-(1-N,N-dimethylcarbamyloxy-2'-methoxybenzyl)imidazole (Compound No. 67)

To a solution of 3.0 g of imidazole in 100 ml THF at 0° C., 17.6 ml of a 2.5M solution of n-butyl lithium in hexane were added over a period of 15 minutes until a light yellow end point. After about 15 minutes, a white precipitate formed. The reaction mixture was stirred for another 45 minutes at 0° C. 6.0 g of 2-methoxybenzaldehyde in 10 ml of THF were added over a period of 10 minutes via syringe. No visible change occurred. The reaction mixture was allowed to warm to room temperature and stirred for two days. 4.7 g of N,N-dimethylcarbamyl chloride were added slowly at room temperature and the reaction mixture was stirred overnight. MgSO$_4$ (3.0 g) was added and the reaction mixture was filtered and rinsed with ethyl acetate. The filtrate was washed with water, dried (MgSO$_4$), filtered and concentrated to an oil. The oil was put onto a silica gel column, and eluted with hexane and then with 100% ethyl acetate to yield 2.5 g of N-(1-N,N-dimethylcarbamyloxy-2'-methoxybenzyl)-imidazole in the form of a white solid.

Example 16

Preparation of N-(1-N,N-dimethylcarbamyloxy-3'-bromobenzyl)imidazole (Compound No. 68)

To a solution of 2.0 g of imidazole in 100 ml THF, at 0° C., 18.8 ml of a 2.5M solution of n-butyl lithium in hexane were added slowly. 3.5 ml of 3-bromobenzaldehyde were added slowly at 0° C. and the reaction mixture was stirred at room temperature overnight. The reaction mixture was cooled to 0° C. and 2.8 ml of N,N-dimethylcarbamyl chloride were added slowly. The reaction mixture was allowed to warm to room temperature and stirred overnight. The mixture was cooled to 0° C. and ice was added. The flask was rinsed with ethyl acetate and the layers separated. The organic layer was washed with saturated aqueous NaHCO$_3$, dried (MgSO$_4$), filtered and concentrated. The product was purified on a silica gel column by elution with ethyl acetate, then THF, and then methanol to yield about 1.5 g of N-(1-N,N-dimethylcarbamyloxy-3'-bromobenzyl)-imidazole as an oil.

Example 17

Preparation of N-(1-trimethylacetoxy-3'-bromobenzyl)-imidazole (Compound No. 69)

The reaction procedure of Example 14 was followed except that 3.7 ml of trimethylacetyl chloride were substituted for the N,N-dimethylcarbamyl chloride. The product was purified on a silica gel column by elution with a 1:1 mixture of hexane and diethyl ether and then 100% diethyl ether to yield 3.5 g of N-(1-trimethylacetoxy-3'-bromobenzyl)-imidazole.

Example 18

Preparation of 4-(1-N-ethylcarbamyloxy-2'-trifluoromethylbenzyl)-3-methylimidazole (Compound No. 70)

(A) To a solution of 2-mercapto-3-methylimidazole in dry THF (100 ml) at 0° C. was added an n-butyl lithium solution (2.5M, 35.1 ml) over 10 minutes. The mixture was allowed to warm to room temperature and stirred for 3 hours. A white solid formed during this time. The temperature was brought down to 0° C. and 2-trifluoromethylbenzaldehyde (7.63 g) was added slowly over 15 minutes. The color turned dark brown. After 30 minutes, water (4 ml) was added to quench the reaction. The mixture was allowed to stir overnight. The 4-(1-hydroxy-2'-trifluoromethylbenzyl)-2-mercapto-3-methylimidazole formed (8.8 g) was collected by filtration, washed with 1:1 diethyl ether:hexanes and air dried.

To a well stirred solution of nitric acid (8 ml) and water (8 ml) was added sodium nitrite (0.93 g). The reaction vessel was cooled externally with a water bath. 4-(1-hydroxy-2'-trifluoromethylbenzyl)-2-mercapto-3-methylimidazole (4.0 g) was added over 5 minutes to the greenish solution. After 1 hour, more sodium nitrite (3.0 g) was added and stirring was continued overnight. Sodium carbonate was added to saturate the mixture. Ethyl acetate was added to dissolve all organic solids. The remaining solid was removed by filtration. Water was added to the filtrate. The layers were separated after being shaken. Removal of water under reduced pressure gave 4-(1-hydroxy-2'-trifluoromethylbenzyl)-3-methylimidazole (2.8 g).

(B) 1.0 g of 4-(1-hydroxy-2'-trifluoromethylbenzyl)-3-methylimidazole was dissolved in 50 ml of THF and the solution was dried (MgSO$_4$) and filtered. 4 drops of DBTL were added to the filtrate, followed by 1.0 g of TEA and 1.0 g of ethyl isocyanate at room temperature. After stirring for 6 hours, the reaction mixture was heated almost to reflux and then subjected to an aqueous work-up. The product was put onto a silica gel column and eluted with ethyl acetate, then THF to yield 0.5 g of 4-(1-N-ethyl-carbamyloxy-2'-trifluoromethylbenzyl)-3-methylimidazole.

Example 19

Preparation of 3-(1-hydroxy-2'-trifluoromethylbenzyl)-4-methyl-5-mercapto-1,2,4-triazole (Compound No. 71)

To a solution of 2.0 g of 3-mercapto-1,2,4-triazole in 80 ml THF at −78° C., 14.0 ml of a 2.5M solution of n-butyl lithium in hexane were added over a period of 10 minutes. The color of the reaction mixture changed to creamy yellow, then to white, half-way through the addition. Stirring was continued at −78° C. for 1 hour and then the temperature was allowed to rise to 0° C. and kept there for one hour. The reaction mixture was cooled again to −78° C. and 1.6 g of 2-trifluoromethylbenzaldehyde were added slowly. The color of the reaction mixture changed to yellow. The reaction mixture was allowed to warm to room temperature and stirred overnight. The resulting orange solution was cooled to 0° C. and about 1 ml of glacial acetic acid was added. A yellow precipitate formed, which was removed by filtration and put onto a silica gel column. Elution with hexane, then a 1:1 mixture of hexane and diethyl ether, and then diethyl ether yielded 1.1 g of 3-(1-hydroxy-2'-trifluoromethylbenzyl)-4-methyl-5-mercapto-1,2,4-triazole in the form of a white solid.

Example 20

Preparation of 3-(1-N-ethylcarbamyloxy-2'-trifluoromethylbenzyl)-4-methyl-5-(N-ethylcarbamylthio)-1,2,4-triazole (Compound No. 72)

To a solution of 1.0 g of 3-(1-hydroxy-2'-trifluoromethylbenzyl)-4-methyl-5-mercapto-1,2,4-triazole (produced according to Example 19) in 25 ml THF, was added 0.7 g of ethyl isocyanate, followed by 15 drops TEA and 2 drops DBTL. The reaction mixture was stirred overnight and then more ethyl isocyanate (1.0 g) and DBTL (2 drops) were added until the reaction was deemed completed. The solvent and excess reagents were removed in vacuo and the residue was purified on a silica gel column by elution with hexane, then methylene chloride, then a 2:1 mixture hexane and ethyl acetate to yield 1.1 g of 3-(1-N- ethylcarbamyloxy-2'-trifluoromethylbenzyl)-4-methyl-5-(N-ethylcarbamylthio)-1,2,4-triazole in the form of a white solid.

Example 21

Preparation of 3-(1-N-ethylcarbamyloxy-2'-trifluoromethylbenzyl)-4-methyl-5-mercapto-1,2,4-triazole (Compound No. 73)

To a solution of 0.5 g of 3-(1-N-ethylcarbamyloxy-2'-trifluoromethylbenzyl-4-methyl-5-(N-ethylcarbamylthio)-1,2,4-triazole (produced according to Example 20) in 25 ml ethanol was added 50 mg of Pd(10%)/C (Lindlar's catalyst). The mixture was stirred under a blanket of hydrogen. After filtering off the catalyst, and removing the solvents, column chromatography yielded 0.4 g of 3-(1-N-ethylcarbamyloxy-2'-trifluorormethylbenzyl)-4-methyl-5-mercapto-1,2,4-triazole.

Example 22

Preparation of 3-(1-trimethylacetoxy-2'-trifluoromethylbenzyl)-4-methyl-1,2,4-triazole (Compound No. 74)

The triazole produced in Example 19 was desulfurized in a manner analogous to that described in Example 18 with respect to an imidazole compound, to produce 3-(1-hydroxy-2'-trifluoromethylbenzyl)-4-methyl-1,2,4-triazole.

0.6 g of 3-(1-hydroxy-2'-trifluoromethylbenzyl)-4-methyl-1,2,4-triazole were dissolved in 20 ml THF, with the aid of sonification. An additional 10 ml THF were added to help dissolve the solid material. The solution was cooled to 0° C. 0.56 g of trimethylacetyl chloride were added slowly and the mixture turned cloudy. After 5 minutes, 0.1 g NaH (60%) added in small portions. The ice/water cooling bath was removed and the reaction mixture was stirred overnight. An additional 0.06 g of NaH was added at room temperature and after another 6 hours, there was no major change. 3 drops of water were added to the cloudy reaction mixture (no hydride was present), followed by diethyl ether. The solid was removed by filtration and washed with diethyl ether. The filtrate was dried (MgSO$_4$), filtered and concentrated to an oil. The oil was purified on a silica gel column by elution with 100% ethylacetate to yield 0.4 g of 3-(1-trimethylacetoxy-2'-trifluoromethylbenzyl)-4-methyl-1,2,4-triazole in the form of an oil.

Example 23

Preparation of 3-(1-N-ethylcarbamyloxy-2'-trifluoromethylbenzyl)-4-methyl-1,2,4-triazole (Compound No. 75)

To a solution of 0.5 g of 3-(1-hydroxy-2'-trifluoromethylbenzyl)-4-methyl-1,2,4-triazole in 30 ml THF at room temperature, 2 drops of DBTDL, then 0.6 g TEA, and then 0.5 g of ethyl isocyanate were added. An additional 0.5 g of ethyl isocyanate were added about 7 hours later and the reaction mixture was stirred overnight. The reaction mixture was then stripped. Hexanes and diethyl ether were added to the residue. The solvents were again removed in vacuo. The oil became solid at a temperature of about 45° C. More hexanes were added and the solid was collected by filtration, rinsed with hexanes, and air-dried to a white solid. This material was put onto a silica gel column, eluted sequentially with methylene chloride, diethyl ether, ethyl acetate, and then THF to yield 0.6 g of the solid 3-(1-N-ethylcarbamyloxy-2'-trifluoromethylbenzyl)-4-methyl-1,2,4-triazole.

Example 24

Preparation of 2-(1-trimethylacetoxy-2'-trifluoromethylbenzyl)-1,2,4-triazole (Compound No. 76)

1.0 g of 1,2,4-triazole was dissolved in 30 ml THF and cooled with a dry ice bath. As the temperature decreased, a solid fell out of the solution. 5.8 ml of a 2.5M solution of n-butyl lithium in hexane were added while keeping the temperature below −30° C. Upon completion of addition of the butyl lithium, the dry ice bath was replaced with an ice water bath and the reaction mixture was stirred at 0° C. to 4° C. for one hour. The reaction mixture was cooled to −70° C. and 2.7 g of 2-trifluoromethylbenzaldehyde was added. The reaction mixture was allowed to warm up to room temperature overnight. 1.8 g of trimethylacetyl chloride were added, dissolving the solid and giving a yellow-white color to the reaction mixture. The reaction mixture was stirred at room temperature for a total of about 3.5 hours. The reaction mixture was then quenched with ice cold water in an ice bath and extracted twice with diethyl ether. The combined organic layers were dried (MgSO$_4$) and concentrated to an oil. The oil was purified on a silica gel column, eluted with a 1:1 mixture of diethyl ether and hexane, to yield about 1.5 g of 2-(1-trimethylacetoxy-2'-trifluoromethylbenzyl)-1,2,4-triazole.

Example 25

Preparation of 2-(1-trimethylacetoxy-2'-chlorobenzyl)-1,2,4-triazole (Compound No. 77)

To a solution of 1.0 g of 1,2,4-triazole in 30 ml THF at 0° C., 0.9 g of NaH (60%) were added. Very little gas was formed, the ice water bath was removed, and the reaction mixture was stirred at room temperature for 3 hours. Then, the reaction mixture was heated to reflux for 2 hours. 2.1 g of 2-chlorobenzaldehyde were added and the reaction mixture was stirred overnight, during which time it turned slightly yellow. 1.8 g of trimethylacetyl chloride were added and the reaction mixture was stirred at room temperature overnight. Water was added and then the reaction mixture was extracted with diethyl ether. The organic layer was dried (MgSO$_4$) and concentrated a yellow oil. The product was put onto a silica gel column, eluted with a 1:1 mixture of diethyl ether and hexane, and yielded 0.5 g of 2-(1-trimethylacetoxy-2'-chlorobenzyl)-1,2,4-triazole.

Example 26

Preparation of 5-(1-hydroxy-2'-trifluoromethylbenzyl)thiazole (Compound No. 78)

To a solution of 5-bromothiazole in 12 ml of ether at −78° C., 2.1 ml of 2.5M n-butyl lithium were added dropwise over 30 minutes. The resulting brown suspension was stirred at −78° C. for 2 hours and then a solution of 2-(trifluoromethyl)benzaldehyde in 2 ml of diethyl ether was added dropwise. The reaction was quenched 1 hour later with 10 ml of water saturated with ammonium chloride. The reaction mixture was extracted twice with 2 ml of diethyl ether. The organic phases were combined, dried (MgSO$_4$) and concentrated in vacuo to yield 1.16 g of a brown oil. This oil was heated to 50° C. at 0.01 mm Hg to remove volatiles leaving 1.16 g of brown oil which was then chromatographed on silica gel using hexane-ethyl acetate (75–25) as the eluant. The last fraction to come off the column contained 297 mg of the desired product, 5-(1-hydroxy-2'-trifluoromethylbenzyl)-thiazole.

Example 27

Preparation of 5-(1-trimethylacetoxy-2'-trifluoromethylbenzyl)thiazole (Compound No. 80)

To a mixture of 102 mg pivaloyl chloride and 19.8 mg of oil free sodium hydride in 0.7 ml THF at 0° C. was added a solution of 142 mg of 5-(1-hydroxy-2'-trifluoromethylbenzyl)thiazole in 0.7 ml THF. Starting material remained after stirring at room temperature for 3 days and heating for 4 hours to 60° C. Another 0.2 ml pivaloyl chloride and 5 mg sodium hydride were added and the reaction mixture heated to 60° C. for 1 hour. Twenty ml of ether were added and the reaction mixture was washed twice with water and once with saturated sodium chloride. The ether was dried (MgSO$_4$), filtered, and evaporated to yield 138 mg of a yellow oil. The crude product was purified via chromatography using silica gel and hexane-ethyl acetate (75:25) as the eluant to yield 5-(1-trimethylacetoxy-2'-trifluoromethylbenzyl)-thiazole.

Example 28

Employing processes similar to those described above, additional compounds, as listed in Tables I, II, IIIa, IIIb, IVa, IVb and V were prepared.

TABLE I

Pyrazines

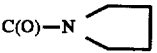

| Compound No. | $Y^1$ | $Y^2$ | $Y^3$ | n | m | R | $R^1$ | $R^2$ | $R^3$ | $R^4$ | $R^5$ |
|---|---|---|---|---|---|---|---|---|---|---|---|
| 1 | H | H | H | 0 | 0 | C(O)N(CH$_3$)$_2$ | CF$_3$ | H | H | H | H |
| 2 | H | H | H | 0 | 0 | C(O)C(CH$_3$)$_3$ | CF$_3$ | H | H | H | H |
| 3 | H | H | H | 0 | 0 | C(O)NHCH$_2$CH$_3$ | CF$_3$ | H | H | H | H |
| 4 | H | H | H | 0 | 0 | C(O)NHCH$_2$CH=CH$_2$ | CF$_3$ | H | H | H | H |
| 5 | H | H | H | 0 | 0 | C(O)NHC(CH$_3$)$_3$ | CF$_3$ | H | H | H | H |
| 6 | H | H | H | 0 | 0 | C(O)—N◁ | CF$_3$ | H | H | H | H |
| 7 | H | H | H | 0 | 0 | C(O)NHCH$_2$CH$_3$ | CH$_3$ | H | H | H | H |
| 8 | H | H | H | 0 | 0 | C(O)NHCH$_2$CH$_3$ | Cl | H | H | H | H |
| 9 | H | H | H | 0 | 0 | C(O)C(CH$_3$)$_3$ | Cl | H | H | H | H |
| 10 | H | H | H | 0 | 0 | C(O)C(CH$_3$)$_3$ | CH$_3$ | H | H | H | H |
| 11 | H | H | H | 0 | 0 | C(O)N(CH$_3$)$_2$ | CH$_3$ | H | H | H | H |
| 12 | H | H | H | 0 | 0 | C(O)N(CH$_3$)$_2$ | Cl | H | H | H | H |
| 13 | H | H | H | 1 | 0 | C(O)NHCH$_2$CH$_3$ | Cl | H | H | H | H |
| 14 | H | H | H | 1 | 0 | C(O)NHCH$_2$CH$_3$ | CH$_3$ | H | H | H | H |
| 15 | H | H | H | 0 | 0 | C(O)NHCH$_2$CH=CH$_2$ | CH$_3$ | H | H | H | H |
| 16 | H | H | H | 0 | 0 | C(O)NHCH$_2$CH=CH$_2$ | Cl | H | H | H | H |
| 17 | H | H | H | 0 | 0 | C(O)N(CH$_3$)$_2$ | CH$_2$CH$_3$ | H | H | H | H |
| 18 | H | H | H | 0 | 0 | C(O)NHCH$_3$ | CH$_2$CH$_3$ | H | H | H | H |
| 19 | H | H | H | 0 | 0 | C(O)NHCH$_2$CH$_3$ | CH$_2$CH$_3$ | H | H | H | H |
| 20 | H | H | H | 0 | 0 | C(O)NHCH$_2$CH=CH$_2$ | CH$_2$CH$_3$ | H | H | H | H |
| 21 | H | H | H | 0 | 0 | C(O)C(CH$_3$)$_3$ | CH$_2$CH$_3$ | H | H | H | H |
| 22 | H | H | H | 0 | 0 | C(O)NHCH$_2$CH$_3$ | F | H | H | H | Cl |
| 23 | H | H | H | 0 | 0 | C(O)NHCH$_2$CH=CH$_2$ | F | H | H | H | Cl |
| 24 | H | H | H | 0 | 0 | C(O)NHCH$_2$CH=CH$_2$ | I | H | H | H | H |
| 25 | H | H | H | 0 | 0 | C(O)NHCH$_2$CH$_3$ | I | H | H | H | H |
| 26 | H | H | H | 0 | 0 | C(O)NHCH$_2$CH$_2$Cl | CF$_3$ | H | H | H | H |
| 27 | H | H | H | 0 | 0 | C(O)NHCH$_2$CH$_2$CH$_3$ | CH$_2$CH$_3$ | H | H | H | H |
| 28 | H | H | H | 0 | 0 | C(O)NHCH$_2$CH$_3$ | Cl | H | H | Cl | H |
| 29 | H | H | H | 0 | 0 | C(O)NHCH$_2$CH=CH$_2$ | Cl | H | H | Cl | H |
| 30 | H | H | H | 0 | 0 | C(O)NHCH$_2$CH=CH$_2$ | OCH$_3$ | H | H | Br | H |
| 31 | H | H | H | 0 | 0 | C(O)N(CH$_3$)$_2$ | OCH$_3$ | H | H | Br | H |
| 32 | H | H | H | 0 | 0 | C(O)C(CH$_3$)$_3$ | OCH$_3$ | H | H | Br | H |
| 33 | H | H | H | 1 | 0 | C(O)NHCH$_2$CH$_3$ | CF$_3$ | H | H | H | H |
| 34 | H | H | H | 0 | 0 | H | CF$_3$ | H | H | H | H |
| 35 | H | H | H | 0 | 0 | H | CH$_3$ | H | H | H | H |
| 36 | H | H | H | 0 | 0 | H | Cl | H | H | H | H |

TABLE II

Pyrimidines

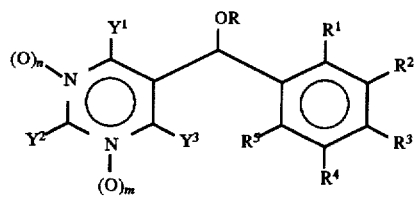

| Compound No. | Y¹ | Y² | Y³ | n | m | R | R¹ | R² | R³ | R⁴ | R⁵ |
|---|---|---|---|---|---|---|---|---|---|---|---|
| 37 | H | H | H | 0 | 0 | H | $CF_3$ | H | H | H | H |
| 38 | H | H | H | 0 | 0 | $C(O)NHCH_2CH_3$ | $CF_3$ | H | H | H | H |
| 39 | H | H | H | 0 | 0 | $C(O)C(CH_3)_3$ | $CF_3$ | H | H | H | H |
| 40 | Cl | H | H | 0 | 0 | $C(O)N(CH_3)_2$ | $CF_3$ | H | H | H | H |
| 41 | Cl | H | H | 0 | 0 | $C(O)N(CH_3)_2$ | $CH_3$ | H | H | H | H |
| 42 | Cl | Cl | H | 0 | 0 | H | $CF_3$ | H | H | H | H |
| 43 | Cl | Cl | H | 0 | 0 | $C(O)C(CH_3)_3$ | $CH_3$ | H | H | H | H |
| 44 | $OCH_3$ | Cl | H | 0 | 0 | H | $CF_3$ | H | H | H | H |
| 45 | $OCH_3$ | $OCH_3$ | H | 0 | 0 | H | $CF_3$ | H | H | H | H |
| 46 | $OCH_3$ | $OCH_3$ | H | 0 | 0 | $C(O)C(CH_3)_3$ | $CF_3$ | H | H | H | H |
| 47 | $OCH_3$ | Cl | H | 0 | 0 | $C(O)N(CH_3)_2$ | $CF_3$ | H | H | H | H |
| 48 | $OCH_3$ | H | H | 0 | 0 | $C(O)N(CH_3)_2$ | $CF_3$ | H | H | H | H |
| 49 | $CH_3$ | H | H | 0 | 0 | $C(O)N(CH_3)_2$ | $CF_3$ | H | H | H | H |
| 50 | $CH_3$ | H | H | 0 | 0 | H | $CF_3$ | H | H | H | H |
| 51 | $CH_3$ | H | H | 0 | 0 | $C(O)C(CH_3)_3$ | $CF_3$ | H | H | H | H |
| 52 | H | H | H | 0 | 0 | H | Cl | H | Cl | H | H |
| 53 | Cl | H | Cl | 0 | 0 | H | $CF_3$ | H | H | H | H |
| 54 | Cl | H | Cl | 0 | 0 | $C(O)NHCH_2CH_3$ | $CF_3$ | H | H | H | H |
| 55 | $OCH_3$ | H | H | 0 | 0 | $C(O)C(CH_3)_3$ | $CF_3$ | H | H | H | H |
| 56 | $CH_3$ | H | H | 0 | 0 | $C(O)NHCH_2CH_3$ | $CF_3$ | H | H | H | H |
| 57 | $CH_3$ | H | H | 0 | 0 | $C(O)NHCH_3$ | $CF_3$ | H | H | H | H |
| 58 | $CH_3$ | H | H | 0 | 0 | $C(O)NHCH_2CH_2Cl$ | $CF_3$ | H | H | H | H |
| 59 | $CH_2CH_3$ | H | H | 0 | 0 | H | $CF_3$ | H | H | H | H |
| 60 | $CH_2CH_3$ | H | H | 0 | 0 | $C(O)C(CH_3)_3$ | $CF_3$ | H | H | H | H |
| 61 | $CH_2CH_3$ | H | H | 0 | 0 | $C(O)NHCH_2CH_3$ | $CF_3$ | H | H | H | H |
| 62 | $CH_2CH_3$ | H | H | 0 | 0 | $C(O)N(CH_3)_2$ | $CF_3$ | H | H | H | H |
| 63 | $CH_2CH_3$ | H | H | 0 | 0 | $C(O)NHCH_3$ | $CF_3$ | H | H | H | H |

TABLE IIIa

Imidazoles

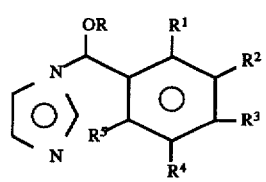

| Compound No. | R | R¹ | R² | R³ | R⁴ | R⁵ |
|---|---|---|---|---|---|---|
| 64 | $C(O)C(CH_3)_3$ | $CF_3$ | H | H | H | H |
| 65 | $C(O)N(CH_3)_2$ | $CF_3$ | H | H | H | H |
| 66 | $C(O)N(CH_3)_2$ | $OCH_3$ | H | H | Br | H |
| 67 | $C(O)N(CH_3)_2$ | $OCH_3$ | H | H | H | H |
| 68 | $C(O)N(CH_3)_2$ | H | Br | H | H | H |
| 69 | $C(O)C(CH_3)_3$ | H | Br | H | H | H |

TABLE IIIb

Imdiazoles

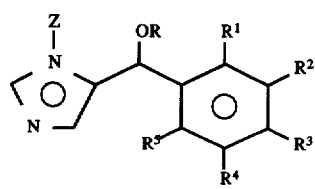

| Compound No. | Z | R | R¹ | R² | R³ | R⁴ | R⁵ |
|---|---|---|---|---|---|---|---|
| 70 | $CH_3$ | $C(O)NHCH_2CH_3$ | $CF_3$ | H | H | H | H |

TABLE IVa

Triazoles

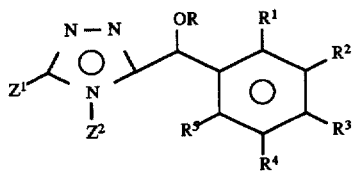

| Compound No. | $Z^1$ | $Z^2$ | R | $R^1$ | $R^2$ | $R^3$ | $R^4$ | $R^5$ |
|---|---|---|---|---|---|---|---|---|
| 71 | SH | $CH_3$ | H | $CF_3$ | H | H | H | H |
| 72 | $SC(O)NHCH_2CH_3$ | $CH_3$ | $C(O)NHCH_2CH_3$ | $CF_3$ | H | H | H | H |
| 73 | SH | $CH_3$ | $C(O)C(CH_3)_3$ | $CF_3$ | H | H | H | H |
| 74 | H | $CH_3$ | $C(O)C(CH_3)_3$ | $CF_3$ | H | H | H | H |
| 75 | H | $CH_3$ | $C(O)NHCH_2CH_3$ | $CF_3$ | H | H | H | H |

TABLE IVb

Triazoles

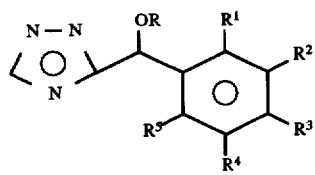

| Compound No. | R | $R^1$ | $R^2$ | $R^3$ | $R^4$ | $R^5$ |
|---|---|---|---|---|---|---|
| 76 | $C(O)C(CH_3)_3$ | $CF_3$ | H | H | H | H |
| 77 | $C(O)C(CH_3)_3$ | Cl | H | H | H | H |

TABLE V

Thiazoles

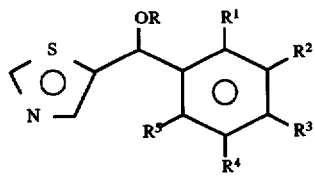

| Compound No. | R | $R^1$ | $R^2$ | $R^3$ | $R^4$ | $R^5$ |
|---|---|---|---|---|---|---|
| 78 | H | $CF_3$ | H | H | H | H |
| 79 | $C(O)N(CH_3)_2$ | $CF_3$ | H | H | H | H |
| 80 | $C(O)C(CH_3)_3$ | $CF_3$ | H | H | H | H |

HERBICIDAL SCREENING TESTS

Compounds listed in the foregoing tables were tested for herbicidal activity by various methods and at various rates of application. The results of some of these tests are given below. As one skilled in the art is aware, the results obtained in herbicidal screening tests are affected by a number of factors that are not readily controllable. Environmental conditions, such as amount of sunlight and water, soil type, soil pH, temperature and humidity, are examples of such factors. Other factors which can affect test results are the depth of planting and the application rate of the herbicide, as well as the nature of the crops being tested. Results will also vary from crop to crop and within the crop varieties.

PRE-EMERGENCE HERBICIDAL SCREENING TEST

On the day preceding treatment, seeds of several different weed species were planted in sandy loam soil at a depth of 0.5 inch (1.3 cm) in individual rows using one species per row across the width of a flat. The soil was fortified with 17-17-17 fertilizer ($N-P_2O_5-K_2O$) on a weight basis and pasteurized. The weeds planted were wild oat (*Avena fatua*) (AVEFA), barnyardgrass (*Echinochloa crusgalli*) (ECHCG), green foxtail (*Setaria viridis*) (SETVI), velvetleaf (*Abutilon theophrasti*) (ABUTH), morningglory species (Ipomoea spp.) (IPOSS), wild mustard (*Sinapsis arvensis*) (SINAR) and yellow nutsedge (*Cyperus esculentus*) (CYPES). Plant densities ranged from 3 to 25 plants per row, depending upon the size of the plants.

Solutions of the test compounds were made by weighing out an appropriate amount of the test compound, for example 74.7 mg for an application rate of 4.0 kg/ha or 18.8 mg for an application rate of 1.0 kg/ha into a 60 ml widemouth bottle, then dissolving the compound in 7.0 ml acetone containing 1% Tween 20® (polyoxyethylene sorbitan monolaurate emulsifier) and then adding 7 ml of deionized water to reach a 14 ml final volume. Tween 20® content was 0.5% v/v of the final spray volume. Additional solvents, not exceeding 2 ml, were used if needed to dissolve the compound.

The soil surface was sprayed inside an enclosed linear spray table. The flats were sprayed with the spray solution calibrated to deliver 748 L/ha. The application rate was between 0.25 and 4.0 kg/ha.

The flats were placed into a greenhouse at 21°–29° C. and watered daily by sprinkling. The degree of weed control was visually assessed and recorded 17–21 days after treatment, as percentage control compared to the growth of the same species of the same age in an untreated check flat.

The results of such pre-emergent testing are summarized in Table VI below.

POST-EMERGENCE HERBICIDAL EVALUATION

The soil was prepared and seeded with the same species and methodology described for the pre-emergence test. The flats were placed in the greenhouse at 21°-29° C. and watered by sprinkling. The seeds of the weed species were planted 10-12 days before treatment. In general, grasses were sprayed at a 3 to 4 leaf stage and broadleaves at a 1 to 2 leaf stage. Watering of the treated flats was confined to the soil surface and not to the foliage of the germinated plants. The degree of weed control was visually assessed and recorded 17-21 days after treatment, as percentage control compared to the growth of the same species in an untreated check flat of the same age.

The results of such post-emergent testing are summarized in Table VII below.

The percent control is the total injury to the plants due to all factors, including inhibited germination, killing of the plant tissue after emergence, stunting, malformation, chlorosis and other types of injury. The control ratings vary from 0 to 100 percent, where 0 represents no effect with growth equal to the untreated control, and 100 represents complete kill; a dash indicates that a test was not performed at that level of application.

TABLE VI

Pre-Emergent - Testing (4.0 kg/ha unless indicated otherwise)

| COMPOUND NO. | AVEFA | ECHCG | SETVI | ABUTH | IPOSS | SINAR | CYPES |
|---|---|---|---|---|---|---|---|
| 1 | 30 | 100 | 100 | 75 | 85 | 50 | 95 |
| 2 | 25 | 100 | 100 | 50 | 90 | 30 | 15 |
| 3 | 60 | 100 | 100 | 90 | 95 | 98 | 100 |
| 4 | 90 | 100 | 100 | 90 | 90 | 80 | 85 |
| 5 | 90 | 100 | 100 | 80 | 90 | 75 | 85 |
| 6 | 15 | 100 | 100 | 90 | 90 | 65 | 75 |
| 7 | 40 | 75 | 100 | 85 | 50 | 75 | 20 |
| 8 | 15 | 75 | 100 | 95 | 40 | 98 | 50 |
| 9 | 10 | 5 | 60 | 0 | 0 | 0 | 0 |
| 10 | 0 | 0 | 50 | 0 | 0 | 0 | 0 |
| 11 | 15 | 98 | 100 | 20 | 85 | 20 | 30 |
| 12 | 25 | 98 | 98 | 60 | 60 | 30 | 60 |
| 13 | 20 | 75 | 100 | 70 | 15 | 15 | 0 |
| 14 | 0 | 10 | 10 | 15 | 15 | 15 | 0 |
| 15 | 20 | 98 | 100 | 50 | 50 | 40 | 25 |
| 16 | 70 | 100 | 100 | 75 | 75 | 70 | 60 |
| 17 | 50 | 100 | 100 | 85 | 90 | 65 | 60 |
| 18 | 70 | 100 | 100 | 100 | 98 | 100 | 95 |
| 19 | 98 | 100 | 100 | 100 | 95 | 100 | 90 |
| 20 | 75 | 100 | 100 | 95 | 98 | 100 | 60 |
| 21 | 30 | 100 | 100 | 10 | 80 | 0 | 5 |
| 22 | 10 | 15 | 85 | 100 | 30 | 100 | 5 |
| 23 | 10 | 25 | 95 | 100 | 40 | 90 | 10 |
| 24 | 85 | 100 | 100 | 80 | 95 | 50 | 85 |
| 25 | 95 | 100 | 100 | 100 | 95 | 75 | 80 |
| 26 | 98 | 100 | 100 | 100 | 95 | 70 | 80 |
| 27 | 80 | 100 | 100 | 100 | 95 | 85 | 80 |
| 28 | 0 | 0 | 0 | 0 | 5 | 10 | 0 |
| 29 | 0 | 0 | 0 | 0 | 0 | 0 | 0 |
| 30 | 0 | 10 | 5 | 0 | 0 | 0 | 0 |
| 31 | 0 | 0 | 10 | 0 | 0 | 0 | 0 |
| 32 | 0 | 0 | 0 | 0 | 0 | 0 | 0 |
| 33 | 20 | 75 | 98 | 60 | 15 | 40 | 25 |
| 34 | 0 | 0 | 5 | 15 | 5 | 5 | 0 |
| 35 | 0 | 0 | 0 | 5 | 5 | 0 | 0 |
| 36 | 0 | 10 | 10 | 20 | 0 | 5 | 0 |
| 37 | 25 | 40 | 98 | 40 | 20 | 30 | 10 |
| 38 | 15 | 100 | 100 | 70 | 90 | 85 | 85 |
| 39 | 20 | 100 | 100 | 40 | 30 | 25 | 5 |
| 40 | 80 | 100 | 100 | 90 | 65 | 98 | 90 |
| 41 | 70 | 100 | 100 | 70 | 70 | 40 | 90 |
| 42 | 0 | 0 | 0 | 0 | 0 | 0 | 0 |
| 43 | 0 | 0 | 0 | 0 | 0 | 0 | 0 |
| 44[a] | 0 | 0 | 0 | 0 | 0 | 0 | 0 |
| 45 | 0 | 0 | 0 | 0 | 0 | 0 | 0 |
| 46 | 0 | 0 | 0 | 0 | 0 | 0 | 0 |
| 47 | 0 | 0 | 0 | 0 | 0 | 0 | 0 |
| 48 | 98 | 100 | 100 | 100 | 95 | 75 | 98 |
| 49 | 85 | 100 | 100 | 98 | 95 | 70 | 98 |
| 50[b] | 0 | 20 | 5 | 10 | 0 | 0 | 3 |
| 51 | 85 | 100 | 100 | 98 | 100 | 90 | 85 |
| 52 | 0 | 0 | 0 | 0 | — | 0 | 0 |
| 53 | 0 | 0 | 0 | 30 | 0 | 5 | 0 |
| 54 | 0 | 95 | 50 | 0 | 0 | 10 | 15 |
| 55[c] | 20 | 100 | 100 | 20 | 15 | — | 0 |
| 56[d] | 40 | 100 | 100 | 80 | 50 | 30 | 75 |
| 58[a] | 95 | 100 | 100 | 98 | 95 | 60 | 90 |
| 59 | 60 | 100 | 80 | 85 | 15 | 60 | 60 |
| 60 | 90 | 100 | 100 | 98 | 98 | 95 | 35 |
| 61[e] | 85 | 100 | 100 | 95 | 95 | 80 | 90 |

TABLE VI-continued

Pre-Emergent - Testing (4.0 kg/ha unless indicated otherwise)

| COMPOUND NO. | AVEFA | ECHCG | SETVI | ABUTH | IPOSS | SINAR | CYPES |
|---|---|---|---|---|---|---|---|
| 62[d] | 98 | 100 | 100 | 100 | 95 | 80 | 100 |
| 64 | 0 | 0 | 10 | 10 | 0 | 0 | 0 |
| 65 | 0 | 5 | 5 | 0 | 0 | 0 | 0 |
| 66 | 70 | 100 | 75 | 0 | 0 | 0 | 0 |
| 67 | 0 | 10 | 10 | 10 | 0 | 5 | 5 |
| 70 | 0 | 10 | 10 | 5 | 0 | 5 | 10 |
| 71 | 0 | 0 | 10 | 0 | 0 | 0 | 0 |
| 72 | 0 | 0 | 10 | 0 | 0 | 0 | 0 |
| 73 | 0 | 0 | 0 | 0 | 0 | 0 | 0 |
| 74 | 0 | 10 | 10 | 0 | 0 | 0 | 0 |
| 75 | 0 | 10 | 0 | 0 | 0 | 0 | 0 |
| 76 | 0 | 0 | 25 | 0 | 0 | 0 | 0 |
| 77 | 0 | 0 | 0 | 0 | 0 | 0 | 0 |
| 78[d] | 0 | 0 | 0 | 0 | 0 | 0 | 0 |
| 79 | 20 | 100 | 98 | 90 | 50 | 40 | 50 |
| 80[d] | 10 | 100 | 100 | 98 | 95 | 70 | 10 |

[a]Applied at 2.0 kg/ha
[b]Applied at 0.5 kg/ha
[c]Applied at 0.25 kg/has
[d]Applied at 1.0 kg/ha
[e]Applied at 0.9 kg/ha

TABLE VII

Pos-Emergent - Testing (4.0 kg/ha unless indicated otherwise)

| COMPOUND NO. | AVEFA | ECHCG | SETVI | ABUTH | IPOSS | SINAR | CYPES |
|---|---|---|---|---|---|---|---|
| 1 | 10 | 85 | 50 | 90 | 80 | 80 | 50 |
| 2 | 15 | 95 | 75 | 30 | 90 | 50 | 60 |
| 3 | 20 | 85 | 80 | 90 | 85 | 80 | 50 |
| 4 | 30 | 90 | 80 | 80 | 90 | 70 | 50 |
| 5 | 40 | 90 | 80 | 75 | 90 | 60 | 60 |
| 6 | 20 | 90 | 85 | 95 | 90 | 70 | 60 |
| 7 | 5 | 15 | 10 | 70 | 75 | 50 | 20 |
| 8 | 10 | 50 | 40 | 60 | 30 | 60 | 10 |
| 9 | 0 | 10 | 20 | 30 | 30 | 20 | 10 |
| 10 | 15 | 85 | 60 | 10 | 40 | 20 | 5 |
| 11 | 15 | 30 | 15 | 50 | 40 | 20 | 30 |
| 12 | 15 | 30 | 60 | 70 | 70 | 30 | 25 |
| 13 | 0 | 5 | 0 | 60 | 15 | 15 | 0 |
| 14 | 0 | 0 | 0 | 15 | 10 | 10 | 0 |
| 15 | 0 | 0 | 10 | 15 | 20 | 15 | 0 |
| 16 | 0 | 30 | 5 | 20 | 10 | 30 | 0 |
| 17 | 5 | 60 | 60 | 60 | 30 | 50 | 30 |
| 18 | 0 | 5 | 10 | 100 | 75 | 75 | 0 |
| 19 | 15 | 75 | 70 | 98 | 60 | 60 | 30 |
| 20 | 5 | 60 | 25 | 75 | 75 | 90 | 0 |
| 21 | 0 | 85 | 90 | 20 | 65 | 5 | 10 |
| 22 | 5 | 0 | 10 | 50 | 20 | 40 | 0 |
| 23 | 5 | 10 | 15 | 50 | 30 | 30 | 0 |
| 24 | 50 | 95 | 90 | 70 | 50 | 40 | 60 |
| 25 | 70 | 98 | 90 | 95 | 90 | 70 | 75 |
| 26 | 30 | 95 | 90 | 75 | 90 | 70 | 50 |
| 27 | 25 | 80 | 95 | 90 | 50 | 60 | 50 |
| 28 | 0 | 10 | 10 | 15 | 10 | 15 | 0 |
| 29 | 0 | 5 | 10 | 15 | 25 | 15 | 0 |
| 30 | 0 | 5 | 5 | 15 | 15 | 40 | 0 |
| 31 | 0 | 0 | 5 | 10 | 15 | 5 | 0 |
| 32 | 0 | 10 | 10 | 10 | 15 | 15 | 0 |
| 33 | 0 | 10 | 10 | 90 | 70 | 50 | 0 |
| 34 | 0 | 0 | 10 | 15 | 25 | 10 | 0 |
| 35 | 5 | 20 | 15 | 30 | 25 | 10 | 0 |
| 36 | 0 | 10 | 15 | 15 | 15 | 15 | 5 |
| 37 | 0 | 0 | 10 | 15 | 50 | 5 | 5 |
| 38 | 10 | 95 | 95 | 80 | 90 | 80 | 80 |
| 39 | 5 | 98 | 90 | 70 | 90 | 50 | 75 |
| 40 | 95 | 98 | 98 | 70 | 80 | 85 | 60 |
| 41 | 75 | 98 | 50 | 60 | 80 | 90 | 60 |
| 42 | 0 | 0 | 0 | 0 | 0 | 0 | 0 |

TABLE VII-continued

Pos-Emergent - Testing (4.0 kg/ha unless indicated otherwise)

| COMPOUND NO. | AVEFA | ECHCG | SETVI | ABUTH | IPOSS | SINAR | CYPES |
|---|---|---|---|---|---|---|---|
| 43 | 0 | 0 | 0 | 0 | 0 | 0 | 0 |
| 44[a] | 0 | 10 | 5 | 5 | 10 | 15 | 0 |
| 45 | 0 | 5 | 5 | 0 | 5 | 5 | 0 |
| 46 | 0 | 0 | 0 | 0 | 5 | 0 | 0 |
| 47 | 0 | 0 | 0 | 20 | 10 | 5 | 0 |
| 48 | 80 | 98 | 90 | 95 | 90 | 65 | 70 |
| 49 | 60 | 90 | 95 | 95 | 90 | 75 | 50 |
| 50[b] | 0 | 0 | 0 | 5 | 20 | 0 | 0 |
| 51 | 10 | 98 | 95 | 90 | 90 | 75 | 15 |
| 52 | 0 | 0 | 0 | 0 | — | 10 | 0 |
| 53 | 0 | 0 | 0 | 0 | 0 | 5 | 0 |
| 54 | 0 | 10 | 5 | 0 | 5 | 10 | 10 |
| 55[c] | 0 | 0 | 0 | 20 | 88 | — | 0 |
| 56[d] | 15 | 5 | 60 | 60 | 70 | 15 | 10 |
| 58[a] | 20 | 25 | 80 | 90 | 90 | 50 | 5 |
| 59 | 5 | 50 | 5 | 70 | 85 | 5 | 40 |
| 60 | 20 | 95 | 90 | 90 | 90 | 70 | 10 |
| 61[a] | 5 | 10 | 60 | 65 | 85 | 10 | 10 |
| 62[d] | 60 | 98 | 90 | 90 | 90 | 30 | 50 |
| 64 | 0 | 5 | 5 | 30 | 30 | 20 | 0 |
| 65 | 5 | 20 | 20 | 60 | 70 | 15 | 5 |
| 66 | 98 | 100 | 98 | 0 | 10 | 10 | 0 |
| 67 | 0 | 0 | 5 | 60 | 20 | 30 | 0 |
| 70 | 0 | 0 | 10 | 90 | 90 | 25 | 5 |
| 71 | 0 | 0 | 0 | 0 | 5 | 0 | 0 |
| 72 | 0 | 0 | 0 | 0 | 5 | 5 | 0 |
| 73 | 0 | 10 | 5 | 0 | 15 | 5 | 0 |
| 74 | 0 | 10 | 15 | 60 | 85 | 40 | 0 |
| 75 | 0 | 15 | 5 | 20 | 25 | 30 | 5 |
| 76 | 0 | 0 | 10 | 0 | 0 | 5 | 0 |
| 77 | 0 | 0 | 5 | 0 | 0 | 5 | 0 |
| 78[d] | 0 | 0 | 5 | 0 | 10 | 0 | 3 |
| 79 | 10 | 25 | 75 | 80 | 90 | 80 | 10 |
| 80[d] | 10 | 50 | 80 | 30 | 90 | 15 | 5 |

[a]Applied at 2.0 kg/ha
[b]Applied at 0.5 kg/ha
[c]Applied at 0.25 kg/has
[d]Applied at 1.0 kg/ha
[e]Applied at 0.9 kg/ha The results above illustrate the preemergent and postemergent efficacy of the present compounds against a variety of grass, broadleaf and perennial weed species.

Although the invention has been described with reference to preferred embodiments and examples thereof, it is not intended that the present invention be limited to only those described embodiments. The description of the preferred embodiments contained herein is intended in no way to limit the scope of the invention. As will be apparent to a person skilled in the art, modifications and adaptations of the above-described invention will become readily apparent without departure from the spirit and scope of the invention, the scope of which is defined and circumscribed by the appended claims.

What is claimed is:

1. A compound of the formula

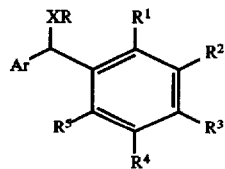

wherein:

Ar is a substituted or unsubstituted pyrimidinyl group;

$R^1$, $R^2$, $R^3$, $R^4$ and $R^5$ are each independently hydrogen, halogen, $C_1$–$C_6$ alkyl, $C_2$–$C_6$ alkenyl, $C_2$–$C_6$ alkynyl, nitro, cyano, hydroxy, thiocyano, —$N(R^{11})(R^{12})$, $C_1$–$C_6$ haloalkyl, $C_1$–$C_6$ haloalkoxy, ($C_1$–$C_6$)alkoxy-($C_1$–$C_6$)alkyl, halo($C_1$–$C_6$)alkoxy-($C_1$–$C_6$)alkyl, —C(X)—$R^{10}$ or —S(O)$_k$—$R^{10}$;

X is oxygen or sulfur;

R is hydrogen, alkyl, alkyl substituted with one or more of halogen or $C_1$–$C_6$ alkoxy or is of the formula —C(Y)—$R^6$, —C(O)—C(O)—$R^6$, —S(O)$_2$—$R^6$ or P(Y)($R^{11}$)($R^{12}$);

wherein:

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S— or is of the formula —$N(R^7)(R^8)$;

wherein $R^7$ and $R^8$ are each independently hydrogen, hydrocarbyl, substituted hydrocarbyl, hydrocarbyloxy, substituted hydrocarbyloxy, ($C_1$–$C_6$)alkoxycarbonyl ($C_1$–$C_6$)alkyl, hydroxycarbonyl($C_1$–$C_6$)alkyl, or $N(R^9)$ ($R^{10}$) wherein $R^9$ and $R^{10}$ are each independently hydrogen, $C_1$–$C_6$ alkyl or phenyl;

$R^{11}$ and $R^{12}$ are each independently $C_1$–$C_6$ alkyl, $C_1$–$C_6$ alkylthio or $C_1$–$C_6$ alkoxy; and k is 0, 1 or 2;

or an agriculturally acceptable salt thereof;
  with the proviso that when R is hydrogen, at least one of $R^1$, $R^2$, $R^3$, $R^4$ and $R^5$ is not hydrogen.

2. A compound as defined in claim 1, or an agriculturally acceptable salt thereof, wherein Ar is a substituted or unsubstituted pyrimidinyl group;
$R^1$, $R^2$, $R^3$, $R^4$ and $R^5$ are each independently hydrogen, halogen, $C_1$–$C_6$ alkyl, $C_1$–$C_6$ haloalkyl, $C_1$–$C_6$ haloalkoxy, nitro or —S(O)$_k$—($C_1$–$C_3$)alkyl wherein k is 0, 1 or 2; and
R is of the formula

wherein $R^6$ is $C_1$–$C_{12}$ alkyl, $C_1$–$C_6$ haloalkyl, phenyl or is $N(R^7)(R^8)$, wherein $R^7$ and $R^8$ are each independently $C_1$–$C_{12}$ alkyl, hydrogen, $C_2$–$C_{12}$ alkenyl, $C_2$–$C_{12}$ alkynyl, $C_1$–$C_{12}$ haloalkyl, $C_1$–$C_6$ alkoxy or $(C_1$–$C_6)$alkoxy$(C_1$–$C_6)$alkyl.

3. A compound as defined in claim 1, or an agriculturally acceptable salt thereof, wherein Ar is a substituted or unsubstituted pyrimidinyl group;
$R^1$ is hydrogen, trifluoromethyl, fluoro, chloro, bromo, iodo, methoxy, methyl or ethyl;
$R^2$, $R^3$, $R^4$ and $R^5$ are each independently hydrogen, chloro or bromo;
R is of the formula

wherein $R^6$ is $C_1$–$C_6$ alkyl or is of the formula $N(R^7)(R^8)$, wherein $R^7$ and $R^8$ are independently hydrogen, $C_1$–$C_6$ haloalkyl, $C_1$–$C_6$ alkyl or $C_2$–$C_6$ alkenyl.

4. A compound as defined in claim 1, or an agriculturally acceptable salt thereof, having the formula

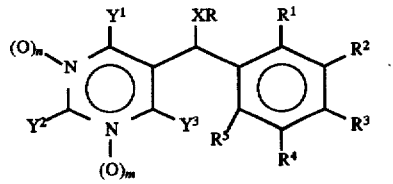

wherein
X, R, $R^1$, $R^2$, $R^3$, $R^4$ and $R^5$ have the same meanings as in claim 1;
$Y^1$, $Y^2$ and $Y^3$ are each independently hydrogen, halogen, $C_1$–$C_6$ alkyl, $C_1$–$C_6$ haloalkyl, $C_1$–$C_6$ alkoxy, $C_2$–$C_6$ alkenyl, $C_2$–$C_6$ alkynyl, mercapto, $C_1$–$C_6$ alkylcarbamylthio, $C_1$–$C_6$ haloalkoxy, nitro, cyano, hydroxy, thiocyano, $(C_1$–$C_6)$alkoxy-$(C_1$–$C_6)$alkyl, —S(O)$_k$—$R^{10}$ or —$N(R^{11})(R^{12})$, wherein k, $R^{10}$, $R^{11}$ and $R^{12}$ have the same meanings as in claim 1; and
n and m are each independently 0 or 1.

5. A compound as defined in claim 1, wherein X is oxygen and R is hydrogen.

6. An herbicidal composition comprising an herbicidally effective amount of a compound according to claim 1, or an agriculturally acceptable salt thereof, and an agriculturally acceptable carrier therefor.

7. An herbicidal composition comprising an herbicidally effective amount of a compound according to claim 2, or an agriculturally acceptable salt thereof, and an agriculturally acceptable carrier therefor.

8. An herbicidal composition comprising an herbicidally effective amount of a compound according to claim 3, or an agriculturally acceptable salt thereof, and an agriculturally acceptable carrier therefor.

9. An herbicidal composition comprising an herbicidally effective amount of a compound according to claim 4, or an agriculturally acceptable salt thereof, and an agriculturally acceptable carrier therefor.

10. An herbicidal composition comprising an herbicidally effective amount of a compound according to claim 5, or an agriculturally acceptable salt thereof, and an agriculturally acceptable carrier therefor.

11. A method for controlling undesirable vegetation comprising applying to an area where control is desired an herbicidally effective amount of a compound according to claim 1, or an agriculturally acceptable salt thereof.

12. A method for controlling undesirable vegetation comprising applying to an area where control is desired an herbicidally effective amount of a compound according to claim 2, or an agriculturally acceptable salt thereof.

13. A method for controlling undesirable vegetation comprising applying to an area where control is desired an herbicidally effective amount of a compound according to claim 3, or an agriculturally acceptable salt thereof.

14. A method for controlling undesirable vegetation comprising applying to an area where control is desired an herbicidally effective amount of a compound according to claim 4, or an agriculturally acceptable salt thereof.

15. A method for controlling undesirable vegetation comprising applying to an area where control is desired an herbicidally effective amount of a compound according to claim 5, or an agriculturally acceptable salt thereof.

* * * * *